(12) United States Patent
Kotoda et al.

(10) Patent No.: US 7,888,555 B2
(45) Date of Patent: Feb. 15, 2011

(54) FLOWER-BUD FORMATION SUPPRESSOR GENE AND EARLY FLOWERING PLANT

(75) Inventors: Nobuhiro Kotoda, Iwate (JP); Masato Wada, Morioka (JP); Junichi Soejima, Morioka (JP)

(73) Assignee: National Agricultural Research Organization, Tsukuba-shi (JP)

( * ) Notice: Subject to any disclaimer, the term of this patent is extended or adjusted under 35 U.S.C. 154(b) by 882 days.

(21) Appl. No.: 11/676,752

(22) Filed: Feb. 20, 2007

(65) Prior Publication Data

US 2007/0180581 A1 Aug. 2, 2007

Related U.S. Application Data

(62) Division of application No. 10/372,909, filed on Feb. 26, 2003, now Pat. No. 7,208,653.

(30) Foreign Application Priority Data

Jun. 20, 2002 (JP) ............................ 2002-180289

(51) Int. Cl.
  C12N 15/29 (2006.01)
  C12N 15/82 (2006.01)
  C12N 5/04 (2006.01)
  A01H 5/00 (2006.01)
  A01H 5/10 (2006.01)

(52) U.S. Cl. .................. 800/286; 800/278; 800/290; 800/298; 536/24.5; 435/419; 435/320.1

(58) Field of Classification Search ................... None
  See application file for complete search history.

(56) References Cited

U.S. PATENT DOCUMENTS 6,307,126 B1 10/2001 Harberd et al.
6,344,601 B1 * 2/2002 Chua et al. ................ 800/290

FOREIGN PATENT DOCUMENTS

WO 97/10339 3/1997
WO 00/71722 11/2000
WO 02/44390 6/2002

OTHER PUBLICATIONS

Hanzawa et al (2005, PNAS 102(21):7748-7753).*
Kotoda et al (2001, Hortscience 36(3):441).*
N. Kotoda, et al., HortScience, vol. 36, No. 3, XP-008028133, p. 441, "The Function Analysis of MdMADS5 and MdTFL, Apple Homologues of APETALA1 and Terminal Flower1, in Transgenic *Arabidopsis*", Jun. 2001.
O. J. Ratcliffe, et al., Development, vol. 125, No. 9, XP-002272108, pp. 1609-1615, "A Common Mechanism Controls the Life Cycle and Architecture of Plants", May 1998.
N. Kotoda, et al., Plant Science, vol. 162, No. 5, XP-002272196, pp. 679-687 "Overexpression of MdMADS5, an APETALA1-Like Gene of Apple, Causes Early Flowering in Transgenic *Arabidopsis*", May 2002.
Merriam Webster Online Dictionary 2005, www.m-w.com/home.html.
Kotoda, et al., 2003, Acta Hort. 625: 337-343.
Zhang, et al., (2005, Plant Science 168:1393-1408).
Bowie, et al., Science 247: 1306-1310, 1990.
McConnell, et al., Nature 411 (6838): 709-713, 2001.
2000 Annual Meeting of the Japanese Society of Plant Physiologists, and the 40th Symposia, Abstracts, vol. 44, p. 170, 2000 w/ attached English Translation.
Montgomery, et al., (Trends in Genetics, Jul. 1998, 14(7): 255-258).
Gutterson, et al., (1995, HortScience 30(5): 964-966).

* cited by examiner

*Primary Examiner*—Stuart F. Baum
(74) *Attorney, Agent, or Firm*—Oblon, Spivak, McClelland, Maier & Neustadt, L.L.P.

(57) ABSTRACT

According to the present invention, a plant having an early flowering property is provided. Specifically, the present invention provides a transformed plant having a gene that suppresses flower-bud formation or the antisense DNA of this gene.

16 Claims, 9 Drawing Sheets

MdTFL
antisense

SEQUENCE LISTING

```
<160> NUMBER OF SEQ ID NOS: 15

<210> SEQ ID NO 1
<211> LENGTH: 772
<212> TYPE: DNA
<213> ORGANISM: Malus domestica

<400> SEQUENCE: 1
cctctctctc tctctctctc tctctctctc tctcttaaaa tgaaaagagc ctcggagcct    60
ctggttgttg ggagagtgat aggagatgtt cttgattcct tcactgcaac aacaaaaatg   120
tctgtcactt acaacaccaa gctagtctgc aatggacttg agctctttcc ttctgttgtc   180
acagccaaac ctagagttga gattcaagga ggggatatga gatctttctt tactttggtg   240
atgaccgacc cagatttccc tggccctagt gatccttatc taagggagca cctgcactgg   300
attgtgacag acattccagg caccacagat gccacatttg gaagagaggt ggtgagttat   360
gagatgccga agcccaacat tggcatccac cggtttgtgt ttgttctttt caagcagaat   420
caaagacaat caatcaacac accttcctcg agggatcact tcagcactcg aagcttcgcg   480
gctgaaaatg acctgggtct tcctgtcgct gccgtctact tcaacgcgca gagagaaact   540
gcagctagaa gacgctagct agtagctcta cccagaactc ctccatccat tatccatata   600
tatgttaaat aaaggcttct ttagagatag gccattgtaa cttttgtttc ccaataacct   660
aaattttaac ttattgacat gtgagaaaat aagtaacacg ttattaatta tttacaatgt   720
atgccacaat attaattatg ttaaattaat tattattacc aaaaataatt at           772

<210> SEQ ID NO 2
<211> LENGTH: 172
<212> TYPE: PRT
<213> ORGANISM: Malus domestica

<400> SEQUENCE: 2

Met Lys Arg Ala Ser Glu Pro Leu Val Val Gly Arg Val Ile Gly Asp
1               5                   10                  15

Val Leu Asp Ser Phe Thr Ala Thr Thr Lys Met Ser Val Thr Tyr Asn
                20                  25                  30

Thr Lys Leu Val Cys Asn Gly Leu Glu Leu Phe Pro Ser Val Val Thr
            35                  40                  45

Ala Lys Pro Arg Val Glu Ile Gln Gly Gly Asp Met Arg Ser Phe Phe
        50                  55                  60
```

```
Thr Leu Val Met Thr Asp Pro Asp Phe Pro Gly Pro Ser Asp Pro Tyr
 65                  70                  75                  80

Leu Arg Glu His Leu His Trp Ile Val Thr Asp Ile Pro Gly Thr Thr
             85                  90                  95

Asp Ala Thr Phe Gly Arg Glu Val Val Ser Tyr Glu Met Pro Lys Pro
            100                 105                 110

Asn Ile Gly Ile His Arg Phe Val Phe Val Leu Phe Lys Gln Asn Gln
        115                 120                 125

Arg Gln Ser Ile Asn Thr Pro Ser Ser Arg Asp His Phe Ser Thr Arg
    130                 135                 140

Ser Phe Ala Ala Glu Asn Asp Leu Gly Leu Pro Val Ala Ala Val Tyr
145                 150                 155                 160

Phe Asn Ala Gln Arg Glu Thr Ala Ala Arg Arg Arg
                165                 170

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (14)..(14)
<223> OTHER INFORMATION: n is inosine

<400> SEQUENCE: 3
aayggncayg aryntttycc                                                  20

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (18)..(18)
<223> OTHER INFORMATION: n is inosine

<400> SEQUENCE: 4
ckytgngcrt traaraanac                                                  20

<210> SEQ ID NO 5
<211> LENGTH: 7
<212> TYPE: PRT
<213> ORGANISM: Artificial Sequence
<220> FEATURE:
<223> OTHER INFORMATION: synthetic peptide

<400> SEQUENCE: 5

Ile Val Thr Asp Ile Pro Gly
1               5

<210> SEQ ID NO 6
<211> LENGTH: 21
<212> TYPE: DNA
<213> ORGANISM: Artificial Sequence
```

```
<220> FEATURE:
<223> OTHER INFORMATION: synthetic oligonucleotide

<400> SEQUENCE: 6
attgtgactg acatcccagg c                                              21

<210> SEQ ID NO 7
<211> LENGTH: 8
<212> TYPE: PRT
<213> ORGANISM: Artificial Sequence
<220> FEATURE:
<223> OTHER INFORMATION: synthetic peptide

<400> SEQUENCE: 7

Val Tyr Phe Asn Ala Gln Arg Glu
1               5

<210> SEQ ID NO 8
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 8
gaccacagat gccacatttg gaa                                            23

<210> SEQ ID NO 9
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 9
gaggtggtga gttatgagat gcc                                            23

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
ttcgagtgct gaagtgatcc ctc                                            23

<210> SEQ ID NO 11
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 11
cagcgacagg aagacccagg tca                                            23

<210> SEQ ID NO 12
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 12
gtacatattg tcgttagaac gcgtaatacg actca                               35
```

```
<210> SEQ ID NO 13
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 13
cgttagacgc gtaatacgac tcactatagg gaga                              34

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
ctcttaaaat gaaaagagcc                                              20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
ttctcacatg tcaataagtt                                              20
```

US 7,888,555 B2

FLOWER-BUD FORMATION SUPPRESSOR GENE AND EARLY FLOWERING PLANT

CROSS-REFERENCE TO RELATED APPLICATION

This application is a divisional of U.S. Ser. No. 10/372,909 (now U.S. Pat. No. 7,208,653), filed on Feb. 26, 2003, which claims a priority from Japanese Patent Application No. 2002-180289 filed Jun. 20, 2002, the disclosure of which is incorporated herein by reference.

BACKGROUND OF THE INVENTION

1. Field of the Invention

The present invention relates to a novel flower-bud formation suppressor gene which is useful to confer an early flowering property on a perennial plant. The present invention also relates to a recombinant vector which comprises a DNA encoding the above gene or an antisense DNA of the gene, a transformant which comprises the recombinant vector, and seeds obtained from the transformant. The present invention further relates to a method for conferring an early flowering property on a plant, and a method for producing an early flowering plant.

2. Description of the Related Art

Unlike for herbaceous plants, it takes a long time for woody plants to progress from flowering to seed-setting, that is, woody plants have long juvenile periods. Hence, improvement through breeding of a perennial fruit tree crop, such as *Malus* (apple) belonging to the family Rosaceae, requires a long period of time. For example, an apple needs a 7 to 8 year-period from sowing to first seed-setting. In breeding of fruit trees, when an agriculturally useful gene, such as a disease-resistant gene of a wild species, is introduced into a cultivar, nearly 10 times of crossing are stochastically essential to obtain a good quality line. Thus, juvenility, the unique feature of woody plants, is a significant factor that impedes the efficiency of cross breeding.

Conventional means to shorten the breeding period of a fruit tree, such as early flowering and seed-setting, use of dwarfing stocks, and training of fruit-bearing mother branch, have been attempted. However, no method can be said to have exerted any landmark effect (Pinero, M. et al., Plant Physiol. 1998, 117: 1-8; Levy, Y. Y. et al., Plant Cell 1998, 10: 1973-1989).

On the other hand, in recent years, several genes regulating flower-bud formation has been isolated from *Arabidopsis thaliana* which is a model plant for Dicotyledon (Ohshima, S. et al., Mol. Gen. Genet. 1997, 254 (2): 186-194; Bradley, D. et al., Science 1997, 275 (5296): 80-83) The molecular mechanism of flower-bud formation is now being elucidated. For example, TERMINAL FLOWER 1 gene (TFL1) has been known to be a gene which is capable of suppressing flower-bud formation (late-flowering genes) (International Patent Publication No. WO 97/10339). In *Arabidopsis thaliana*, it has been experimentally shown that overexpression of the gene causes late flowering, and suppressed expression thereof causes early flowering (Ratcliffe, O. J. et al., Development 1999, 126: 1109-1120; Liljegren, S. J. et al., Plant Cell 1999, 11: 1007-1018). However, genes having a similar sequence with TFL1 but having a reverse effect are also known. So it has not been easy to clarify the genes and mechanisms involved in the flowering (Weigel, D. et al., Nature 1995, 377: 495-500; Mandel, M. A. et al., Nature 1995, 377: 522-524).

Moreover, neither a gene nor a protein involved in the flower-bud formation in Rosaceous plants including the genus *Malus* has been shown to date.

Further in the field of agriculture, attempts, such as to confer an early flowering property on perennial crops by regulating genes that suppress flower-bud formation, have not been reported so far.

SUMMARY OF THE INVENTION

An object of the present invention is to isolate a gene relating to flower-bud formation in perennial plants, and to provide a plant having an early flowering property by transforming a plant using the gene or an antisense DNA of the gene.

We have succeeded in cloning a novel TERMINAL FLOWER 1-like gene from an apple plant, as a result of thorough studies to achieve the above objects. Specifically, the present invention is based on the findings that the above novel gene was actually confirmed to have an activity for suppressing flower-bud formation in *Arabidopsis thaliana* and *Malus* x *domestica*, and that a regenerated plant conferred with an early flowering property can be produced by transforming plant cells with a vector DNA having an antisense DNA of the above gene incorporated therein, allowing the cells to form a callus, allowing the callus to grow, allowing to re-differentiate to a plant, and then grafting the plant to a rootstock.

The present invention provides an isolated protein comprising an amino acid sequence represented by SEQ ID NO: 2.

Also, the present invention provides an isolated protein comprising an amino acid sequence having deletion, substitution or addition of one or several amino acids in an amino acid sequence represented by SEQ ID NO: 2, and having flower-bud formation-suppressing activity.

Further, the present invention provides an isolated nucleic acid or a fragment thereof which comprises a nucleotide sequence represented by SEQ ID NO: 1, or which is capable of hybridizing under stringent conditions to a DNA comprising a sequence complementary to at least a part of nucleotide sequence represented by SEQ ID NO: 1 and which encodes a protein having flower-bud formation-suppressing activity.

The present invention provides an antisense nucleic acid, which comprises a sequence complementary to the nucleotide sequence of the above isolated nucleic acid or the fragment thereof.

Furthermore, the present invention provides a recombinant vector, which comprises either at least a part of the above isolated nucleic acid or the fragment thereof, or at least a part of the above antisense nucleic acid.

Further, the present invention provides a transformant, which comprises the above recombinant vector. The transformant may be preferably a plant or plant cells, more preferably a perennial plant or cells thereof. The perennial plant preferably used in the present invention includes a perennial fruit tree. The transformant may have an early flowering property.

The present invention also provides a seed, which is obtained from the above transformant.

Still further, the present invention provides a method for conferring an early flowering property on a plant, which comprises suppressing an expression or an activity of an endogenous MdTFL gene in a plant.

Also, the present invention provides a method of regulating the time to flowering of a plant, which comprises introducing the above isolated nucleic acid or the fragment thereof or the above antisense nucleic acid into a plant.

Further, the present invention provides a method for producing an early flowering plant, which comprises the steps of constructing a recombinant vector comprising the above isolated nucleic acid or the fragment thereof or the above antisense nucleic acid, transforming a host plant with the recombinant vector, and regenerating a plant from the obtained transformant.

In the above methods, the plant is preferably a perennial plant, particularly a perennial fruit tree.

BRIEF DESCRIPTION OF THE DRAWINGS

FIGS. 6A and 6B show line 705-1 at 8 months and at 12 months after grafting, respectively. "f" in FIG. 6A indicates a flower, and "gt" indicates a grafted site. FIG. 6C shows line 705-4 at 11 months after grafting. FIG. 6D is a photograph showing a morphological comparison of leaves from each line (lines 303-3 and 705-1, and wild type). FIG. 6E shows flower buds formed at the shoot tip in the growth stage. FIG. 6F is a photograph showing an enlarged view of photograph of FIG. 6E and the arrow indicates a differentiated flower bud.

DETAILED DESCRIPTION OF THE INVENTION

Figure 1:
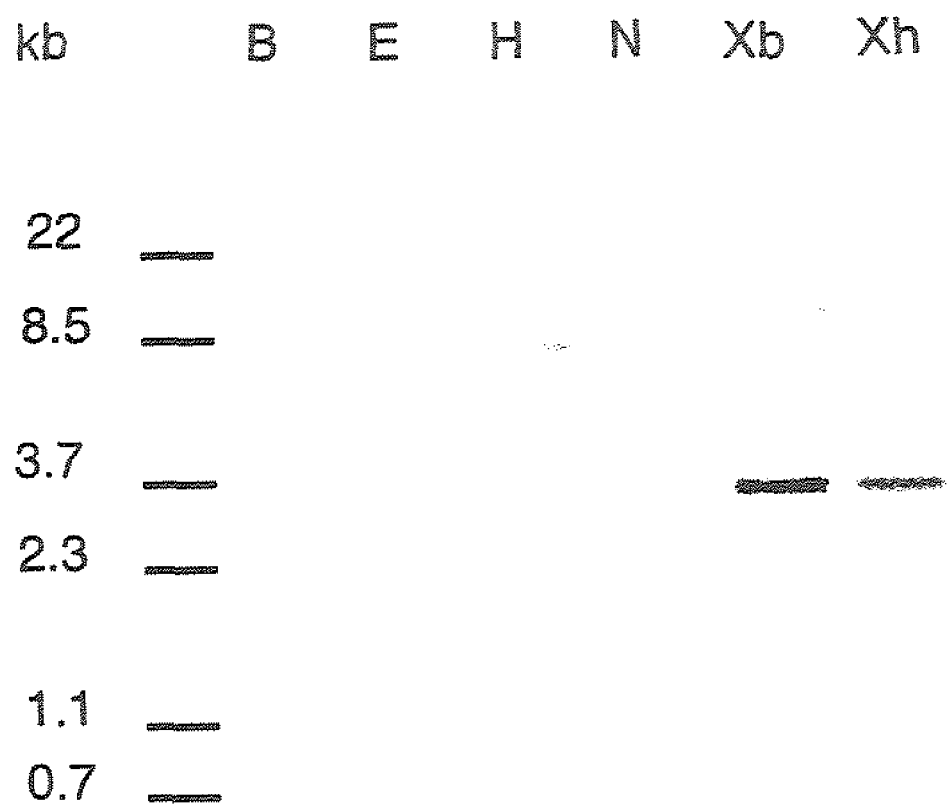
FIG. 1 provides a photograph showing the MdTFL gene in non-transformed apple plants, as detected by the Southern blotting. Each alphabet letter on the lane represents a restriction enzyme: B, BamHI; E, EcoRI; H, HindIII; N, NcoI; Xb, XbaI; and Xh, XhoI.

We have isolated a novel gene relating to flowering, TERMINAL FLOWER 1 (TFL1)-like gene as described below. To isolate a gene encoding TFL1 homologous protein derived from a plant belonging to the family Rosaceae, particularly to the genus Malus, we first obtained a gene fragment by performing polymerase chain reaction (PCR) using degenerate primers that were designed on the basis of highly-conserved amino acid sequences among TFL1-like proteins derived from other plants and using as a template cDNA derived from the shoot apex of an apple plant. Then, we amplified the full-length cDNA by rapid amplification of cDNA ends polymerase chain reaction (RACE-PCR), thereby finding a novel TFL1-like gene. In addition, the gene has some extent of homology (approximately 75%) with TERMINAL FLOWER 1 (TFL1) gene of Arabidopsis thaliana. For Rosaceous plants, since the gene has been isolated for the first time from an apple (Malus x domestica), it is referred to as MdTFL (Malus x domestica TFL1). Further, the present inventors have confirmed that the gene has an activity for suppressing flower-bud formation in Malus x domestics. According to the present invention, the time to flowering of a plant having MdTFL gene introduced therein is regulated by promoting or suppressing the expression of this MdTFL gene.

The MdTFL gene is involved in the suppression of flower-bud formation in Rosaceous plants. Thus, a plant transformed to suppress the expression of endogenous MdTFL gene or the activity of endogenous MdTFL protein will exhibit early flowering as a result of the inhibited activity to suppress flower-bud formation.

As a technique to suppress gene expression, an antisense method which introduces the antisense DNA of a gene and RNA interference (RNAi) are known, for example. Specifically, in the antisense method, expression of a target gene is suppressed by specifically binding the antisense sequence to a sequence of the target gene. The antisense sequence inhibits the expression of a target gene through the blocking of translation or transcription by binding itself to cellular mRNA or genomic DNA. RNA interference utilize an event that when a double-stranded RNA is present in a cell, an endogeneous mRNA which is complementary to the sequence of the double-stranded RNA is degraded and destructed, and as a result, the gene expression is specifically suppressed in the cell (Hannon, G J., Nature 2002, 418: 244-251 (review); Elbashir, S M. et al., Nature 2001, 411: 494-498; McCaffrey, A P. et al., Nature 2002, 418: 38-39). There is also another technique which utilizes co-suppression. Co-suppression is a phenomenon in a plant, for example, when a gene is introduced into a plant by ligating the gene downstream of a promoter which causes constant and strong expression in a sense orientation, thereby causing the expression of both the introduced gene and the endogenous gene to be suppressed (Montgomery, M K and Fire, A (1998), Trends Genet., 14, 255-8).

According to the present invention, a plant exhibiting early flowering property is produced by introducing either the MdTFL gene, or an antisense DNA of the gene regulated by a strong promoter into a plant, thereby suppressing the expression of the endogenous MdTFL gene, and inhibiting activity to suppress flower-bud formation.

On the other hand, the introduction of the MdTFL gene in a sense direction into a plant normally results in enhanced expression of the MdTFL gene. In such a case, flower-bud formation-suppressing activity is thereby enhanced, and the plant exhibits late flowering. Such a plant having a capacity for late flowering is useful in studying the suppression mechanism of flower-bud formation.

Alternatively, as well-known in the art, an antibody against the MdTFL protein may be useful for suppressing the activity of the MdTFL protein.

Isolation of the MdTFL gene, production of the MdTFL protein, preparation of a recombinant vector, and production of a transformant will be described below in detail.

1. Isolation and Identification of the MdTFL Gene (1) Preparation of mRNA and cDNA Library MdTFL gene can be obtained by any known method using mRNA purified from RNA extracted from the tissue of a Rosaceous plant. Examples of known methods include RACE (rapid amplification of cDNA ends) -PCR, RT-PCR and screening from cDNA library. The MdTFL gene is expressed mainly in plant leaves, shoot apices, calices and the like. Hence, examples of a source of mRNA include a part (tissue) of a plant, such as Rosaceous plant leaves or shoot apices. Further, Rosaceous plant tissues (for example, epidermis, phloem, parenchyma, xylem, bundle, palisade tissue and spongy tissue) sterilely cultured in a medium, such as MS media (Murashige and Skoog media), or tissue culture cells (for example, a callus) can also be used. Examples of a plant that is used as a source for gene isolation in the present invention are not specifically limited, as long as it is a plant belonging to the Rosaceae family. Specific examples are as shown below.

The genus *Malus*: *Malus* x *domestics*, *Malus baccata* var. *mandschurica*, *Malus sieboldii*, *Malus prunifolia* var. *ringo* ASAMI The genus *Rosa*: *Rose hybrida*

The genus *Prunus*: *Prunus persica*, *Prunus avium*, *Prunus amygdalus*

The genus *Pyrus*: *Pyrus pyrifolia*, *Pyrus communis*

The genus *Fragaria*: *Fragaria* x *ananassa*

The genus *Cydonia*: *Cydonia oblonga*

The genus *Rubus*: *Rubus palmatus* mRNA can be prepared, for example, by any conventional technique after freezing the shoot apex portion of a Rosaceous plant with liquid nitrogen. For example, the frozen plant is crushed in a mortar or the like, and then a crude RNA fraction is extracted and prepared from the resulting crushed product by a cesium chloride method, a cetyl trimethyl acetyl bromide (CTAB) method or the like. Next, from the crude RNA fraction, poly(A) $^+$RNA (mRNA) can be obtained by an affinity column method using oligo dT-cellulose as carriers, a method using oligo dT-immobilized latex particles or the like.

Using the thus obtained mRNA as a template, a single-stranded cDNA is synthesized with oligo dT 20 and reverse transcriptase using a commercially available kit (for example, cDNA Synthesis Kit (STRATAGENE)). Then, a double-stranded cDNA is synthesized from the single-stranded cDNA. Subsequently, an appropriate adaptor or a cassette (for example, EcoRI cassette manufactured by TAKARA) is added to the obtained double-stranded cDNA, so that a cDNA library can be prepared as, for example a template for RACE-PCR. As a kit to perform the RACE-PCR method, for example, 3'-Full RACE Core Set (TAKARA) or 5'-Full RACE Core Set (TAKARA) can be used.

(2) Preparation of MdTFL Gene Fragments

An example of a method for cloning the MdTFL gene involves clarifying unknown DNA regions by RACE-PCR using fragments of the gene, ultimately amplifying the full-length cDNA by PCR, and then cloning the amplified product containing the gene into an appropriate vector.

MdTFL fragments can be obtained by PCR using degenerate primers designed from a consensus sequence of TFL1 from *Arabidopsis thaliana* (GenBank Accession number: U77674) and CENTRORADIALIS from *Antirrhinum majas* (CEN gene: GenBank Accession number: S81193). In PCR, an example of a template DNA that can be used according to the invention is a genomic DNA from a Rosaceous plant or the cDNA library obtained in (1) above. In addition, examples of degenerate primers include a sense primer of 5'-AAT/CGGI-CAT/CGAA/GT/CTITTT/CCC-3' (SEQ ID NO: 3) and an antisense primer of 5'-CG/TT/CTGIGCA/GTTA/GAAA/GAAIAC-3' (SEQ ID NO: 4). In the sequence, "I" indicates inosine. However, primers in the present invention are not limited to these sequences. Appropriate primers can be designed by a person skilled in the art based on the above consensus sequence.

(3) Isolation of MdTFL Gene

Two gene-specific sense primers and two gene-specific antisense primers are respectively designed for an appropriate region in the MdTFL fragment obtained in (2) above. To elucidate an unknown sequence on the 5' of the gene, 2 antisense primers and 2 cassette primers; and to elucidate an unknown sequence on the 3' of the gene, 2 sense primers and 2 cassette primers are used to perform RACE-PCR. As a result, a DNA fragment containing the 5' upstream or the 3' downstream of the MdTFL gene is obtained. For 5'-RACE, the primer is designed to be a specific sequence of about 20 bp on the 3' of the gene fragment obtained in (2) above. For 3'-RACE, the primer is designed to be a specific sequence of about 20 bp on the 5' of the gene fragment obtained in (2) above.

Subsequently, a primer having a specific 5' upstream sequence and a primer having a specific 3' downstream sequence are prepared. PCR is performed using these primers, so that MdTFL cDNA can be amplified. The primers are designed as about a 20 bp specific sequence in the 5' upstream region obtained in 5'-RACE, and as a specific sequence in 3' downstream region (poly A excluded) obtained in 3'-RACE. As a template for PCR, the cDNA library obtained in (1) above can be used.

After the MdTFL gene obtained in (3) above is ligated to, for example, pBluescript plasmid vector having T-end added to its EcoRV site, and *Escherichia coli* or the like is transformed with the vector, the gene can be cloned.

Specific examples of a vector that can be used herein include pUC18, pUC119, pBR322 and the like, in addition to a plasmid pBluescript. Normally, a PCR product tends to have adenine (A) to its end. Hence, the PCR product of a gene can be easily cloned by cleaving a vector with a restriction enzyme, such as EcoRV, which causes blunt-ends, and then adding thymine (T) end to the vector (TA cloning method). Ligation of the PCR product of the gene to a plasmid pBluescript treated to add T-end may be normally performed by reacting them using, for example, Ligation kit (TAKARA) at generally 16° C. for 1 hour.

Transformation of *Escherichia coli* can be performed by any known method. When pBluescript is used as a vector, the resulting transformant becomes ampicillin-resistant, and at the same time, insertion of a foreign gene into a region encoding β-galactosidase causes deletion of β-galactosidase activity. Thus, white, ampicillin-resistant colonies which cannot hydrolyse X-GAL can be selected as transformants (Blue-White selection). In this way, a transformant having plasmid pBMDTFL 12 wherein MdTFL gene is incorporated into a vector plasmid pBluescript can be obtained. For example, when the gene is introduced into *Escherichia coli* JM109, *Escherichia coli* JM109 (pBMDTFL 12) can be obtained as a transformant.

Further, a transformed microorganism, such as *Escherichia coli* having the above plasmid pBMDTFL 12, is cultured, and then a known means, such as an alkali-SDS method, is employed, so that a large amount of plasmid pBMDTFL12 having MdTFL gene incorporated therein can be obtained.

(4) Genetic Analysis

Using plasmid vector pBMDTFL12 obtained in (3) above, the entire nucleotide sequence of MdTFL is determined. The nucleotide sequence can be determined by any known technique, such as the Maxam-Gilbert chemical modification method or a dideoxy nucleotide chain termination method. Normally, a nucleotide sequence is determined using an automatic DNA sequencer (for example, SQ-5500 DNA sequencer manufactured by Hitachi, Ltd.).

SEQ ID NO: 1 exemplifies the nucleotide sequence of the MdTFL gene of the present invention, and SEQ ID NO: 2 exemplifies an amino acid sequence of a protein encoded by the MdTFL gene (hereinafter, referred to as "MdTFL protein"). However, different plant varieties may differ in their amino acid sequences to some extent. Further, even if plants are of the same variety, they differ in their amino acid sequences, because amino acids can be altered by, for example, mutation. Accordingly, the present invention also encompasses a protein comprising an amino acid sequence having deletion, substitution or addition of one or several amino acids (for example, 1 to 10 amino acids, preferably 1 to 8, more preferably 1 to 3 amino acids) in an amino acid sequence represented by SEQ ID NO: 2, and having flower-bud formation-suppressing activity.

For example, the MdTFL protein of the present invention encompasses an amino acid sequence comprising an amino acid sequence having deletion of 1 to 10, preferably 1 to 5 amino acids; addition of 1 to 10, preferably 1 to 5 amino acids; or substitution of 1 to 10, preferably 1 to 5 amino acids with other amino acids. Such protein having a mutation may be prepared using an appropriate method and selected for its flower-bud formation-suppressing activity.

Further, the protein according to the present invention encompass a peptide fragment of the protein described above. Such peptide fragment may be useful, for example for producing an antibody or a fragment thereof directed to the protein of the present invention.

The term "flower-bud formation-suppressing activity" in the present invention refers to the capability to cause late flowering by suppressing flower-bud formation. This activity can be confirmed by introducing the gene that is thought to have the activity into a model plant, such as *Arabidopsis thaliana*, or tobacco, and then examining the time to flowering.

Furthermore, the MdTFL gene of the present invention also encompasses a gene which is capable of hybridizing under stringent conditions, to a sequence complementary to at least a part of DNA sequence comprising the nucleotide sequence of the above MdTFL gene, and which encodes a protein having flower-bud formation-suppressing activity. In the present invention, the terms "gene" and "nucleic acid" are sometimes used interchangeably. Stringent conditions mean those under which specific hybrids are formed, while unspecific hybrids are not formed. For example, DNA having high homology (homology of 76% or more, preferably 80% or more) with a certain nucleic acid hybridizes to the nucleic acid under such conditions. More specifically, an example of such conditions includes a sodium concentration of 300 to 2000 mM, preferably 600 to 900 mM, and a temperature of 40 to 75° C., preferably 65° C. For example, under hybridization conditions including sodium concentration of 500 mM and a temperature of 65° C., when hybridization of DNA to be tested with certain nucleic acid is confirmed by standard techniques, such as the Southern blotting or dot-blot hybridization, it can be said that the DNA is capable of hybridizing under stringent conditions to the certain nucleic acid.

The term "a part of sequence" used herein means a nucleotide sequence of DNA containing a portion of the nucleotide sequence of the above MdTFL gene, and encoding a protein having flower-bud formation-suppressing activity.

Further, the present invention encompasses a fragment of the gene of the present invention described above. Such fragment may be not specifically limited, as long as it is at least a part of the gene of the present invention. The fragment may be used, for example for preparing a probe or primers of the gene of the present invention.

Once the nucleotide sequence of the MdTFL gene of the present invention is determined, the MdTFL gene of the present invention can be obtained by chemical synthesis, PCR using cDNA or genomic DNA of the gene as a template, or hybridization using, as a probe, a DNA fragment containing the nucleotide sequence.

The nucleotide sequence of the MdTFL gene of the present invention and the amino acid sequence of MdTFL have been registered with DDBJ under Accession number AB052994.

(5) Analysis of the Number of Copies of MdTFL Gene and Expression Site in Plant Tissue The number of copies of the MdTFL gene in a Rosaceous plant can be confirmed by extracting DNA from the plant cells or tissues, according to standard methods, and then subjecting the DNA to Southern analysis. By analyzing the number of copies of MdTFL gene and the expression sites in this way, the characteristics of TFL1-like gene having a tendency to form a gene family can be studied.

Moreover, the expression of MdTFL gene in plant tissues can be confirmed by analyzing expression of mRNA or by analyzing the expression of the protein in each tissue of Rosaceous plant. Specific examples of a method for confirming expression of the MdTFL gene of the present invention include RT-PCR, Northern analysis and the like. Examples of a method for confirming the expression of MdTFL protein include Western analysis using an antibody against MdTFL protein, and the like. Identification of the expression pattern of MdTFL gene enables clarification of the characteristics of the MdTFL gene, so that it is useful in elucidation of the functions of the MdTFL gene.

2. Production of MdTFL Protein

The MdTFL protein of the present invention can be produced from cells or tissues of the above-described Rosaceous plant by any method known in the technical field for purifying proteins. Further, MdTFL protein of the present invention can also be produced by a chemical peptide synthesis method known in the technical field, such as a solid-phase synthesis method. Furthermore, MdTFL protein of the present invention can also be produced by culturing a transformant obtained by transformation with DNA encoding the MdTFL protein, and collecting the protein from the resulting culture. Such a process for producing protein using genetic engineering techniques is well-known in the art, and is described in detail below.

(1) Preparation of Vector

A recombinant vector for transformation can be obtained by ligating the MdTFL gene to an appropriate vector. A transformant can be obtained by introducing the recombinant vector into a host so that the MdTFL gene can be expressed in the host.

As a vector, a phage or a plasmid which is capable of autonomously replicating in a host is used. Examples of a plasmid DNA include a plasmid derived from *Escherichia coli* (for example, pBR322, pUC18 and pUC19), a plasmid derived from *Bacillus subtilis* (for example, pUB110 and pTP5), and a plasmid derived from yeast (for example, YEp13, YEp24 and YCp50). Examples of a phage DNA include λ phages (for example, λgt10, λgt11 and, λZAP). Furthermore, animal virus vectors, such as retroviruses or vaccinia viruses, and insect virus vectors, such as baculoviruses can also be used.

An example of a method employed for inserting the MdTFL gene into a vector, involves cleaving a purified DNA with an appropriate restriction enzyme, and then inserting the cleaved product into a restriction site or a multi-cloning site of an appropriate vector DNA for ligation to the vector.

It is necessary that MdTFL gene be incorporated into a vector, in such a way that the function of the gene is exerted. Hence, in addition to a promoter and the MdTFL gene, cis elements, such as an enhancer, splicing signal, poly A addition signal, a selection marker, ribosome binding sequence (Shine-Dargarno (SD) sequence) and the like can be ligated to a recombinant vector, if necessary. Examples of a selection marker include a dihydrofolate reductase gene, an ampicillin resistance gene and a neomycin resistance gene. In addition to a vector which is capable of autonomously replicating in two or more types of host microorganisms, such as $Escherichia$ $coli$ or yeast, various shuttle vectors can also be used. Such vectors can also be cleaved with the above restriction enzyme to obtain the linear vector.

To ligate a DNA fragment to a linear vector, any known DNA ligase can be used. The DNA fragment and the linear vector are ligated to each other after annealing, so that a recombinant vector is prepared.

(2) Transformation

A host to be used for transformation is not specifically limited, as long as it can express MdTFL gene. Examples of such host include bacteria ($Escherichia$ $coli$, $Bacillus$ $subtilis$ and the like), yeast, plant cells, animal cells (COS cells, CHO cells and the like), and insect cells.

When bacteria are used as hosts, preferably a recombinant vector is capable of autonomously replicating in the bacteria host, and comprises a promoter, ribosome binding sequence, the MdTFL gene and transcription termination sequence. In addition, a gene that regulates a promoter may be included. An example of an $Escherichia$ $coli$ host is $Escherichia$ $coli$ DH5α, and an example of $Bacillus$ host is $Bacillus$ $subtilis$. Any promoter which is capable of expressing in a host, such as $Escherichia$ $coli$, can be used. For example, a promoter derived from $Escherichia$ $coli$ or a phage, such as trp promoter, lac promoter, $P_L$ promoter, or $P_R$ promoter is used. For example, tac promoter or the like which is artificially designed and altered can also be used. Examples of a method for introducing a recombinant vector into bacteria are not specifically limited, as long as the methods are for introducing DNA into bacteria, and include a method using a calcium ion and an electroporation.

When yeast is used as a host, for example, $Saccharomyces$ $cerevisiae$ and $Schizosaccharomyces$ $pombe$ are generally used. In this case, a promoter to be used herein is not specifically limited, as long as it can be expressed in yeast. Examples of such a promoter that can be used herein include GAL1 promoter, GAL10 promoter, heat-shock protein promoter, GAP promoter and ADH promoter. Examples of a method for introducing a recombinant vector into yeast are not specifically limited, as long as they are methods for introducing DNA into yeast, and include an electroporation, a spheroplast method and a method using lithium acetate.

When animal cells are used as hosts, examples of the animal cells used herein include simian cells COS-7, Vero, Chinese hamster ovary cells (CHO cell), mouse L cells, rat GH3 and human FL cells. As a promoter, SRα promoter, SV40 promoter, CMV promoter or the like is used. In addition, an early gene promoter of human cytomegalovirus may also be used. Examples of a method for introducing a recombinant vector into animal cells include an electroporation, a calcium phosphate method and a lipofection.

When insect cells are used as hosts, Sf9 cells or the like are used. Examples of a method for introducing a recombinant vector into insect cells include a calcium phosphate method, a lipofection and an electroporation.

(3) Production of MdTFL Protein

In the present invention, the MdTFL protein can be obtained by culturing the above transformant carrying the MdTFL gene, and collecting the protein from the culture. The term "culture" means any of the culture supernatant, cultured cells, cultured bacterial strain, or disrupted cells or disrupted bacteria. The transformant of the present invention is cultured in a culture medium according to methods normally employed for culturing hosts.

As a culture medium for culturing the transformants obtained using host microorganisms, such as $Escherichia$ $coli$, yeast or the like, either natural or synthetic medium can be used, as long as it contains a carbon source, a nitrogen source, inorganic salts and/or others that are assimilable by microorganisms, and allows efficient culturing of transformants.

Examples of a carbon source that is used herein include: carbohydrate, such as glucose, fructose, sucrose or starch; organic acid, such as acetic acid or propionic acid; and alcohols, such as ethanol or propanol. Examples of a nitrogen source that is used herein include: inorganic acid, such as ammonia, ammonium chloride, ammonium sulfate, ammonium acetate or ammonium phosphate; and ammonium salt of organic acid; peptone, meat extract, corn steep liquor, and other nitrogen-containing compounds. Examples of inorganic substances that are used herein include potassium primary phosphate, potassium secondary phosphate, magnesium phosphate, magnesium sulfate, sodium chloride, ferrous sulfate, manganese sulphate, copper sulfate and calcium carbonate.

Culturing is normally performed by shaking culture, aeration-agitation culture or the like under aerobic conditions at approximately 37° C. for approximately 5 to 30 days. While culturing, pH is maintained at around neutral pH. pH is adjusted using inorganic or organic acid, alkali solution or the like. While culturing, antibiotics, such as ampicillin or tetracycline may be added into the medium, if necessary.

When a microorganism transformed with an expression vector containing an inducible promoter is cultured, an inducer may be added into the medium, if necessary. For example, when a microorganism transformed with an expression vector containing Lac promoter is cultured, isopropyl-β-D-thiogalactoside (IPTG) or the like may be added as an inducer, and when a microorganism transformed with an expression vector containing trp promoter is cultured, indoleacetic acid (IAA) may be added into the medium.

As a culture medium for culturing transformants obtained using animal cells as hosts, generally employed RPMI1640 medium, DMEM medium or the medium supplemented with fetal calf serum or the like are used. Culturing is normally performed in the presence of 5% $CO_2$, at 37° C. for approximately 1 to 30 days. While culturing, antibiotics such as kanamycin, penicillin may be added into the culture medium, if necessary.

After culturing, when the MdTFL protein is produced within bacterial strains or within cells, the protein is extracted by disrupting the strains or the cells. In addition, when the MdTFL protein is secreted from the bacterial strains or the cells, the culture medium may be used intact, or the culture medium may be subjected to centrifugation or the like to remove the strains or the cells. Subsequently, the MdTFL protein can be isolated and purified from the above culture by using a biological method alone, or an appropriate combination thereof generally employed for protein isolation and purification, such as ammonium sulfate precipitation, gel chromatography, ion exchange chromatography, affinity chromatography.

Whether or not MdTFL protein is obtained can be confirmed by SDS-polyacrylamide gel electrophoresis or the like.

3. Preparation of Recombinant Vector and Production of Transformed Plant

The MdTFL gene or the antisense DNA of the MdTFL gene obtained as described in the above section "1. Isolation and identification of MdTFL gene" is introduced into host plants, so that expression of the MdTFL gene is either enhanced or suppressed, and the flower-bud formation time can be regulated. For example, a transformed plant having an early flowering property can be produced by suppressing the expression of the MdTFL gene in the host plant. On the other hand, a transformed plant having a late flowering property can be produced by enhancing the expression of the MdTFL gene. As described above, a transformed plant wherein the expression of the MdTFL is regulated can be used for studying the flower-bud formation and flowering properties of a plant.

The term "early flowering property" in the present invention means a time period from the germination or grafting of a plant to the first flowering, which is shorter than that of a control plant (non-transformant). In addition, the term "a late flowering property" means a time period from the germination or grafting of a plant to the first flowering which is longer than that of a control plant.

(1) Host Plant for Transformation

Host plants in the present invention mean any of the following: plant cultured cells, the whole cultivated plant, plant organs (for example, leaves, flower petals, stalks, roots, root stocks and seeds) or plant tissues (for example, epidermis, phloem, parenchyma, xylem and fibrovascular bundle). Preferably, a plant that can be used as a host plant may be, but not specifically limited to, perennial plants or trees, when the purpose of the present invention which is to confer an early flowering property on plant species having long juvenile periods is taken into consideration, in addition to the model plant, *Arabidopsis thaliana*. The term "perennial plant" does not mean a plant which ends its life within a year, such as rice or wheat, but means a plant which can grow for several years (5 to 10 years or more) (perennial). An example of a perennial plant is a plant having fruits (fruit tree plant). Such perennial fruit plant includes a plant belonging to the Rosaceae family (apples, pears, peaches, cherry fruits or the like), a plant belonging to the Ebenaceae family (persimmons or the like), a plant belonging to the Vitaceae family (grapes or the like), a plant belonging to the Rutaceae family (a plant belonging to the genus *Poncirus, Fortunella, Citrus* or the like), a plant belonging to the Ericaceae family (blueberries, cranberries or the like), a plant belonging to the Juglandaceae family (walnuts or the like) and a plant belonging to the Fagaceae family (chestnuts or the like). As a tree, for example, plants belonging to the Taxodiaceae (cryptomerias or the like), Pinaceae (*Pinus densiflora, Pinus thunbergii* or the like) and Cupressaceae (Japanese cypress or the like) families are included.

(2) Recombinant Vector

A recombinant vector containing the MdTFL gene or the antisene DNA of the gene can be obtained by ligating (inserting) the gene or the antisense DNA into an appropriate vector. Examples of a vector for insertion of the MdTFL gene or the antisense DNA of the gene are not specifically limited, as long as they are capable of replicating in host plants, and include a plasmid DNA, a phage DNA and a binary vector system.

Examples of a plasmid DNA include a plasmid derived from *Escherichia coli* (for example, pBR322, pUC18 and pUC19), and a plasmid derived from *Bacillus subtilis* (for example, PBU110 and pTP5). Examples of a phage DNA include λ phages (for example, λgt10, λgt11 and λZAP). In addition, when transformation is performed using an *Agrobacterium* (as will hereinafter be described in detail), a binary vector system (for example, pBI121, pGA482 and pSMAK251) can be used.

The MdTFL gene can be obtained as described in the above section "1. Isolation and identification of MdTFL gene." Further, as the antisense DNA (nucleic acid) of MdTFL gene, DNA (nucleic acid) comprising a sequence complementary to the nucleotide sequence represented by SEQ ID NO: 1 can be exemplified. However, the antisense DNA (nucleic acid) used in the present invention is not required to be a sequence completely complementary to the nucleotide sequence represented by SEQ ID NO: 1, as long as it can suppress the expression of the endogenous MdTFL gene when introduced into a host plant. Therefore, a DNA (nucleic acid), which comprises a sequence complementary to a DNA that is capable of hybridizing under stringent conditions to a DNA comprising a sequence complementary to at least a part of the nucleotide sequence represented by SEQ ID NO: 1, can also be used as an antisense DNA in the present invention. Furthermore, an antisense nucleic acid may be a part of a sequence complementary to the nucleotide sequence represented by SEQ ID NO: 1, as long as it can suppress or inhibit the expression (translation or transcription) of the endogenous MdTFL gene when introduced into a host plant.

Stringent conditions and a method for synthesizing DNA are as described in the section, "1. Isolation and identification of MdTFL gene."

For example, a method employed to insert MdTFL gene or the antisense DNA of the gene into a recombinant vector involves cleaving purified DNA with an appropriate restriction enzyme, ligating an appropriate linker thereto if necessary, and then inserting the cleaved DNA into a restriction site or a multi-cloning site of an appropriate vector DNA for ligation to the vector.

The MdTFL gene or the antisense DNA of the gene should be incorporated into a vector, so that it can exert its function. Thus, an expression cassette is ligated in the vector. The expression cassette comprises (i) a promoter sequence which can direct transcription of the DNA within plant cells, (ii) the MdTFL gene or the antisense DNA of the gene ligated downstream of the promoter sequence, and (iii) a terminator sequence containing a sequence required for transcription termination and polyadenylation, and added downstream of the gene or the antisense DNA. In addition to a promoter, a DNA sequence for further promoting transcription, for example, cis elements, such as an enhancer sequence, splicing signal, poly A addition signal, a selection marker, a ribosome binding sequence (SD sequence) may also be ligated to the expression cassette.

A promoter to be used herein is not specifically limited, as long as it is active in a plant. For example, a promoter for use in permanent expression, such as 35S promoter, or an inducible promoter can also be used.

Further, a terminator to direct transcription termination can also be ligated downstream of the MdTFL gene or the antisense DNA of the gene, if necessary. Such terminator includes Cauliflower mosaic virus-derived terminator and nopaline synthase gene terminator. However, a terminator to be used herein is not limited to the above terminators, as long as it is known to be active in a plant.

Furthermore, it is preferable to ligate an effective selection marker gene to a recombinant vector in order to effectively select transformed plants of interest. Examples of a selection marker used for this purpose include a kanamycin resistance gene (NTP II), hygromycin phosphinothricin acetyltransferase (htp) gene which confers, onto a plant, resistance to the antibiotic, hygromycin, and a phosphinothricin acetyltransferase (bar) gene which confers, onto a plant, resistance to bialaphos.

(3) Production of Transformant

The transformed plant of the present invention can be obtained by introducing the recombinant vector described in (2) above into a host plant so that the MdTFL gene or the antisense DNA of the gene ligated to the vector can function.

The above recombinant vector can be introduced into a host plant by various known methods. For example, an indirect introduction method using Agrobacteria and a direct introduction method represented by an electroporation, a method using polyethylene glycol, a particle gun method and the like can be employed. Among these methods, the method using Agrobacteria is very effective for dicotyledons including Rosaceous plants, because the method ensures stable transformation.

When the *Agrobacterium* method is employed, for example, a constructed recombinant vector is introduced into appropriate *Agrobacterium* strains, such as *Agrobacterium tumefaciens* C58, LBA4404, EHA101, C58C1Rif$^R$, EHA105 or the like or *Agrobacterium rhizogenes* LBA9402 or the like using a method including freezing and thawing method, or an electroporation. Subsequently, the strain is allowed to infect aseptically-cultured lamina according to a conventional method such as floral dip method, or a leaf disc method, so that transformed plants can be obtained. In addition, examples of an *Agrobacterium* infection method include a method using an intermediate vector and a binary vector. In the present invention, a gene can be introduced using any of these infection methods.

When the particle gun method is employed, a plant, plant organ or plant tissue may be used directly, or after preparing sections thereof, or after preparing protoplasts therefrom. The thus prepared samples can be treated using a gene transfer system (for example, particle gun PDS-1000, Bio-Rad). Treatment conditions may differ depending on types of a plant or a sample; however, normally pressure of approximately 450 to 2000 psi is applied from around 4 to 12 cm away from the subject.

When plant cultured cells are used as hosts, transformation is performed by introducing recombinant vectors into the cultured cells by the particle gun method, the electroporation method or the like.

In terms of recombinant efficiency and ease of handling, production of a transformed plant by the *Agrobacterium* infection method using a binary vector system will be specifically described below as a preferred example of the present invention.

When introducing a gene by the *Agrobacterium* infection method, it requires a step of infecting a host plant with *Agrobacteria* having a plasmid containing a target gene. When this step is performed by the floral dip method, host plants to be transformed are allowed to grow, and the flower buds of the host plants are directly dipped into a suspension of *Agrobacterium* strains having plasmids containing the MdTFL gene or the antisense DNA of the gene. The pots are transferred onto a tray, covered, and then allowed to stand overnight while maintaining humidity. The covers are removed on the next day, and the plants are further allowed to grow, thereby harvesting seeds. Next, to select a plant having the transgene (transformant), seeds derived from various lines are inoculated on MS agar media supplemented with appropriate antibiotics. The plants that have grown on the media are transplanted to pots for further growth. Thus, seeds of transformed plants into which the MdTFL gene or the antisense DNA of the gene of the present invention has been introduced can be obtained.

On the other hand, a leaf disc method is preferably employed for infection with Agrobacteria when perennial plants are used as hosts, because a large number of transformants can be directly produced by this method. Specifically, leaf discs collected from sterilely cultured sterile leaves of plants of the genus *Malus* are dipped in a culture of, for example, *Agrobacterium tumefaciens* EHA101 (pSMDTFL, see EXAMPLE 4), cultured in regeneration media, and allowed to form calli and to grow. As a regeneration medium, for example, a known medium, such as an MS medium supplemented with plant hormone can be used. Then, calli are selected using selection media for selection. As a selection medium for selecting transformants, the above regeneration medium which is further supplemented with, for example, kanamycin of 25 to 100 μg/mL, may be used, or as a medium for sterilizing Agrobacteria, the same regeneration medium which is supplemented with an antimicrobial agent, such as cefotaxime of 200 to 500 μg/mL, may be used.

Calli, shoots, hairy roots or other tissues resulting from transformation can be used for cell culture, tissue culture or organ culture. Alternatively, these tissues or cells can be allowed to regenerate into plant by any known standard method for culturing plant tissues by administering a plant hormone (for example, auxin, cytokinin, abscisic acid and gibberellin) at an appropriate concentration. Furthermore, acclimation of transformed plants is performed by transplanting the transformed plant to rooting media for the plants to form their own roots, and then transplanting the plants into pots with soil. Alternatively, naturalization is performed by grafting the plants to appropriate rootstocks. Accordingly, transfer from cultivation at laboratory level to greenhouse level becomes possible.

Whether or not the MdTFL gene or the antisense DNA of the gene is introduced into a plant can be confirmed by a PCR, the Southern hybridization, the Northern hybridization or the like. For example, DNA is prepared from transformed plants, DNA-specific primers are then designed, and PCR is subsequently performed using a conventional method. Then, transformation can be confirmed by subjecting amplified products to agarose gel electrophoresis, polyacrylamide gel electrophoresis, capillary electrophoresis or the like, staining the products using an appropriate dye, such as ethidium bromide and SYBR Green, and then detecting the amplified product as a single band. In addition, amplified products can also be detected by performing PCR using primers labeled with a suitable label, for example fluorescent dye. Furthermore, other methods that can also be employed herein involves binding amplified products to a solid phase, such as a microplate, and then confirming the amplified products by fluorescence, enzyme reaction or the like.

(4) Expression Analysis of MdTFL Gene in Transformed Plant

Analysis of expression level and expression site of the MdTFL gene in the transformed plant having MdTFL gene or the antisense DNA of the gene introduced therein can be performed by extracting mRNA from these cells or tissues by any known method in the technical field, and the mRNA of the MdTFL gene can be detected by any known RT-PCR method or Northern analysis.

The transformed plant having the enhanced expression of the MdTFL gene can be used for studying flower-bud formation and flowering of plants. Moreover, the transformed plant having suppressed expression of the MdTFL gene is of great value in agriculture, because it exhibits an early flowering property.

4. Early Flowering Plant

The transformed plant produced according to the above section "3. Preparation of recombinant vector and production of transformed plant" having suppressed expression of the MdTFL gene exhibits an early flowering property. On the other hand, the transformed plant, produced by the same, having enhanced expression of the gene exhibits a late flowering property. Alternatively, a plant on which is conferred an early flowering property can be obtained by suppressing expression or activity of an endogenous MdTFL in a plant. Therefore, a method of producing an early flowering plant is not limited to the methods described herein in detail. Such method can be easily understood by a person skilled in the art.

Evaluation on the time to flowering of a plant including the transformed plant described above (for example, an early flowering property or a late flowering property) can be performed by cultivating, under similar conditions, a plant to be tested (for example, transformed plants having MdTFL gene or the antisense DNA of the gene introduced therein) and control plant (for example, non-transformed plants), and comparing their times to flowering. For example, in the case of the model plant, *Arabidopsis thaliana*, the transformed plants are planted into pots supplemented with soil containing vermiculite and perlite, allowed to grow at 20 to 25° C., and then examined for their times to flowering. In the case of perennial plants, the shoots transformed with the above aseptic culture system are grafted for acclimation, and the plants are transferred into a greenhouse and then examined for their times to flowering.

Furthermore, using the above procedures for differentiation and induction of plant from infected cells, tissues (for example, roots, shoots and leaves) or organs (for example, vegetative point and pollen) of transformed plants are cultured. Thus, without a reproductive phase (seed), transformed plants can be reproduced. Such techniques and procedures are known to a person skilled in the art, and general methods of tissue culturing are described by various kinds of experimental manuals.

The seed obtained from the thus produced transformed plant of the present invention also germinates and grows normally, and exhibits an early flowering property. This confirms that the introduced MdTFL gene or the antisense DNA of the gene is conserved in the next generation, so that the above early flowering property is stably inherited in the progenies. Therefore, according to the present invention, practical and useful plants exhibiting an early flowering property can be obtained.

According to the present invention, a plant having a gene that suppresses flower-bud formation or an antisense DNA of this gene is provided. The transformed plant having the antisense DNA obtained according to the present invention has an early flowering property and an early seed-setting property, and causes no malformation, so that it is useful in agriculture.

EXAMPLES

The present invention is further illustrated by the following non-limiting examples:

Example 1

Isolation of MdTFL Gene (1) Apple Plant Employed in the Following Experiments 15 to 16-year old Jonathan apples (*Malus* x *domestics* cv. Jonathan) grafted to Maruba rootstocks were used.

(2) Preparation of Poly (A)$^+$ RNA

Before and after floral initiation stage (differentiation of flower-bud), that is, from July to September, the shoot apices of the plant of (1) above were collected, and then total RNA was prepared by the CTAB method. Specifically, 3 g of frozen apple shoot apex was crushed into a powdery form, suspended in a 3 mL of 2×CTAB solution (2% CTAB, 0.1 M Tris-HCl, pH 9.5, 20 mM EDTA, 1.4 M NaCl, 1% 2-propanol), and then incubated at 65° C. for 10 minutes. The solution was subjected twice to extraction using chloroform isoamyl, added with ¼ volume of 10 M lithium chloride, and then allowed to stand at −20° C. for 2 hours to obtain precipitated RNA. Subsequently, centrifugation is performed at 12,000×g for 10 minutes 4° C. to collect the precipitated RNA.

The obtained total RNA was dissolved in TE (10 mM Tris-HCl (pH 8.0), 1 mM EDTA), and then subjected to TE saturation phenol treatment, phenol/chloroform treatment, and then ethanol precipitation, thereby obtaining purified total RNA. The obtained total RNA was dissolved in sterilized water, and then subjected to an absorbance measurement method and a formaldehyde denatured agarose gel electrophoresis method, thereby confirming that high quality total RNA had been prepared.

140 µg of the above total RNA was dissolved in 235 µl of sterilized water. 35 µl of oligotex (dT) 30 (TOYOBO) was added to the solution, the solution was heated at 70° C. for 10 minutes, and then rapidly cooled in ice. 17.5 µl of 5M NaCl was added to the solution, the solution was stirred, and then heated at 37° C. for 10 minutes. Subsequently, the solution was centrifuged at 12,000×g for 5 minutes at 25° C., and then the supernatant was discarded. 500 µl of a washing buffer (10 mM Tris-HCl (pH 7.5), 1 mM EDTA, 0.5 M NaCl, 0.1% SDS) was added to the solution, and then the solution was centrifuged again at 12,000×g for 5 minutes at 25° C. After 100 µl of distilled water was added to the precipitate and the solution was heated at 65° C. for 5 minutes, the solution was centrifuged at 12,000×g for 10 minutes 25° C. The supernatant was stored, and then 100 µl of distilled water was added again to the precipitate. The solution was heated at 65° C. for 5 minutes and then centrifuged at 12,000×g for 10 minutes at 25° C. The supernatant was collected, and then added to the supernatant obtained in the first step. Subsequently, ethanol precipitation was performed to obtain 3.0 µg of poly (A)$^+$ RNA.

(3) Synthesis of cDNA Library

Single-stranded cDNA was synthesized by a cDNA synthesis kit (Amersham) using 3.0 µg of the poly (A)$^+$ RNA obtained in (2) above. In this reaction, oligo (dT) 25 was used as a primer. A mixed solution of the RNA and the primers was prepared with the following composition.

| | |
|---|---|
| RNA | 30 μl (3 μg) |
| Primer | 3 μl |
| Total | 33 μl |

The above mixture was heated at 70° C. for 5 minutes. Then, the mixture was placed on ice for 1 minute, and then the following reagents were added to the mixture.

| | |
|---|---|
| Mixed solution of RNA/primer | 33 μl |
| 5× buffer for first strand synthesis reaction | 12 μl |
| Phosphoric acid | 3 μl |
| HPRI (human placental RNase inhibitor) | 3 μl |
| NTP mix for first strand | 6 μl |
| Total | 57 μl |

3 μl (20 units/μl) of reverse transcriptase was added to the above solution, and then the solution was incubated at 42° C. for 2 hours, thereby synthesizing a single-stranded cDNA. Next, the following reagents were added to the reaction solution of the resulting single-stranded cDNA.

| | |
|---|---|
| Single-stranded cDNA reaction solution | 60 μl |
| 2.5× buffer for second strand synthesis | 120 μl |
| 0.8 units/μl RNase H | 3 μl |
| 3.5 units/μl DNA polymerase I | 20 μl |
| Sterile distilled water | 97 μl |
| Total | 200 μl |

The above reaction solution was incubated at 12° C. for 1 hour, 22° C. for 1 hour, and then 70° C. for 10 minutes, so that double-stranded cDNA was synthesized. The synthesized double-stranded cDNA was incubated using 6 units of T4 polymerase at 37° C. for 10 minutes to obtain cDNA with blunt-ends. After phenol/chloroform extraction and ethanol precipitation were performed, the resulting pellet was dissolved in 20 μl of TE buffer. 3 μl of cDNA solution (1.0 μg) was mixed with 1 μl (100 pmol) of EcoRI adaptor, 4 μl of ligation kit solution II and 8 μl of ligation kit solution I (TAKARA), and then the mixed solution was incubated at 4° C. for 12 hours to add EcoRI ends to the cDNA. After phosphorylation of EcoRI ends, 4.0 μl (500 μg) of the cDNA solution having EcoRI ends, 1.0 μl of EcoRI cassette (TAKARA), 5 μl of a ligation kit solution II, and 10 μl of a ligation kit solution I (TAKARA) were mixed, and then the mixed solution was incubated at 4° C. for 12 hours to add EcoRI cassette to the double-stranded cDNA, thereby preparing cDNA library for RACE-PCR cloning.

(4) Preparation of Primers

Primers were synthesized based on a highly-conserved amino acid sequence among the TFL1 protein of *Arabidopsis thaliana* and CENTRORADIALIS (CEN) protein of *Antirrhinum majas*. Specifically, a primer 5'-ATTGTGACTGA-CATCCCAGGC-3' (SEQ ID NO: 6) was synthesized as a 5' sense primer based on IVTDIPG (SEQ ID NO: 5) on the N-terminal, the common sequence of the TFL-like proteins of both plants. Further, a degenerate primer 5'-CG/TT/CT-GIGCA/GTTA/GAAA/GAAIAC-3' (SEQ ID NO: 4) was synthesized as 3' antisense primer based on VYFNAQRE (SEQ ID NO: 7) on the C terminal. In the above sequence, "I" indicates inosine.

(5) Amplification of the Apple MdTFL Gene Fragment by RT-PCR

PCR was performed using as a template the double-stranded cDNA synthesized in (2) above, and as primers the sense primer and antisense primer prepared in (3) above. The composition of PCR reaction solution is as shown below.

| | |
|---|---|
| cDNA solution | 1 μl |
| Sterile distilled water | 17.5 μl |
| 10× PCR buffer | 2.5 μl |
| 2.5 mM dNTP mix | 2 μl |
| 10 μM sense primer | 1 μl |
| 10 μM antisense primer | 1 μl |
| 5 U/μl Taq polymerase | 0.25 μl |
| Total | 25.25 μl |

The above reaction solution was mixed well, and then heated at 95° C. for 10 minutes. PCR was performed 40 cycles with each cycle consisting of the following conditions: thermal denaturation at 94° C. for 1 minute, annealing at 50° C. for 1 minute, and elongation reaction at 72° C. for 2 minutes.

The resulting PCR product was subjected to 1.5% agarose gel electrophoresis. As a result, so that a single band of 235 bp was confirmed. The PCR product was ligated to pBluescript SKII (+) (STRATAGENE) that had been cleaved with EcoRV and added with thymine (T) end to construct a recombinant plasmid. The recombinant plasmid was transformed into *Escherichia coli* strain DH5α. A single colony was cultured in an LB medium, plasmids were purified and then analyzed by an automated fluorescent DNA sequencer (Hitachi, Ltd. SQ5500) using the Thermo Sequenase premixed cycle sequence kit (Amersham). Determination of the nucleotide sequences of a plurality of PCR products revealed that they were all identical in sequence and showed homology (approximately 75%) with *Arabidopsis thaliana* TFL1. Therefore, the gene fragments were considered as parts of the TFL homologous gene of the apple plant.

(6) Isolation of the Apple MdTFL Gene

The full-length MdTFL gene was isolated by performing RACE-PCR using the cDNA library prepared in (3) above and the gene fragment prepared in (5) above. Specifically, within the gene fragment obtained in (5) above, two sense primers (R1S and R2S) (SEQ ID NOS: 8 and 9, respectively) having specific DNA sequences for the gene, and two antisense primers (R1A and R2A) (SEQ ID NOS: 10 and 11, respectively) having specific DNA sequences were designed. 5' RACE- and 3' RACE-PCR were performed using these 4 primers and cassette primers (C1 and C2) (SEQ ID NOS: 12 and 13, respectively) (TAKARA). In the 5' RACE, the first PCR was performed using the cDNA library as a template and C1 and R2A as primers, and the second PCR was performed using the PCR product obtained from the first PCR as a template and C2 and R2A as primers. On the other hand, in the 3' RACE, the first PCR was performed using cDNA library as a template and C1 and R1S as primers, and the second PCR was performed using the PCR product obtained from the first PCR as a template and C2 and R2S as primers.

Reaction Composition of PCR is as Follows.

| | |
|---|---|
| cDNA solution/the PCR product from 1st PCR | 1 μl |
| Sterile distilled water | 17.5 μl |
| 10× PCR buffer | 2.5 μl |

-continued

| | |
|---|---|
| 2.5 mM dNTP mix | 2 µl |
| 10 µM cassette primer | 1 µl |
| 10 µM specific primer | 1 µl |
| 5 U/µl LA Taq polymerase | 0.25 µl |
| Total | 25.25 µl |

The reaction solution was mixed well. The first and second PCR reactions were both performed 30 cycles with each cycle consisting of the following conditions: thermal denaturation at 94° C. for 30 seconds, annealing and extension at 62° C. for 4 minutes An amplification product of 550 bp was obtained from 5' RACE-PCR, and that of 450 bp was obtained from 3' RACE-PCR. By the method described in (5) above, each gene fragment was cloned, and then the nucleotide sequences were determined. It was shown that ATG, a translation initiation site was present in a 550 bp fragment of the 5' upstream of the gene, and poly A sequence was present in a 450 bp fragment of the 3' downstream. Accordingly, specific primers (2S and 2A) (SEQ ID NOS: 14 and 15, respectively) were designed within each of the gene fragments, and then the full-length MdTFL gene was amplified by LA-PCR. PCR reaction was performed 25 cycles with each cycle consisting of the following conditions: thermal denaturation at 94° C. for 1 minute, annealing at 50° C. for 1 minute and elongation reaction at 72° C. for 2 minutes. By the above-mentioned procedures, 650 bp of the amplified gene fragment was obtained. Subsequently, the gene fragment was cloned by the method described in (5) above, thereby obtaining four recombinant plasmids, pBMDTFL1, pBMDTFL2, pBMDTFL5 and pBMDTFL12, respectively The reaction composition for PCR is as follows.

| | |
|---|---|
| cDNA solution | 1 µl |
| Sterile distilled water | 17.5 µl |
| 10× PCR buffer | 2.5 µl |
| 2.5 mM dNTP mix | 2 µl |
| 10 µM sense primer | 1 µl |
| 10 µM antisense primer | 1 µl |
| 5 U/µl LA Taq polymerase | 0.25 µl |
| Total | 25.25 µl |

(7) Determination of Nucleotide Sequence

Using the plasmids pBMDTFL1, pBMDTFL2, pBMDTFL5 and pBMDTFL12, the entire nucleotide sequence of the obtained cDNA was determined. The plasmids were prepared from cultured *Escherichia coli* cells by an alkali-SDS method. The nucleotide sequence was determined by a method similar to that in (5) above. The result showed that any cDNA in the plasmids pBMDTFL1, pBMDTFL2, pBMDTFL5 and pBMDTFL12 comprised nucleotides of 656 bp (SEQ ID NO: 1), and only one open reading frame encoding a putative protein which comprises 172 amino acid residues was present in the nucleotides.

Example 2

Southern Blot Analysis of MdTFL Gene (1) Preparation of Genomic DNA

From the leaves of an apple plant "Jonathan apple," genomic DNA was prepared by a CTAB method. Specifically, 3 g of apple leaves were frozen in liquid nitrogen, and then quickly crushed in mortar to obtain a powder form. To remove sugars, an extraction buffer (10% polyethylene glycol 6000, 0.35 M sorbitol, 0.1 M Tris-HCl pH 7.5, 1% 2-mercaptoethanol) was added and mixed well in a 50 mL tube. Then, centrifugation was performed at 12,000×g for 5 minutes at room temperature. The supernatant was discarded, and then to the pellet 9 mL of a lytic buffer (0.35 M sorbitol, 0.1 M Tris-HCl pH 7.5, 1% 2-mercaptoethanol) and 1 mL of 10% sarcosine were added, followed by gentle agitation at room temperature for 10 minutes. Then, 10 mL of 2×CTAB (2% CTAB, 0.1 M Tris-HCl pH 9.5, 20 mM EDTA, 1.4 M NaCl, 1% 2-mercaptoethanol) was added, and then the solution was gently shaken at 56° C. for 20 minutes.

After the above CTAB solution was treated twice with chloroform/isoamyl, an equivalent amount of 2-propanol was added to obtain white precipitate. The DNA fiber was collected by winding it to a glass rod, dissolved in 5 mL of 1 M NaCl solution, and then subjected to RNase digestion treatment (10 mg/mL) at 56° C. for 2 to 3 hours. Subsequently, the resulting solution after digestion was subjected to ethanol precipitation, and then dissolved in 1 mL of TE to obtain genomic DNA.

(2) Hybridization

10 µg of the genomic DNA obtained in (1) above was digested with BamHI, EcoRI, HindIII, NcoI, XbaI and XhoI, and the digest product was subjected to 0.8% agarose electrophoresis. After running, DNA fragments were transferred to a nylon membrane. The membrane was immersed in a prehybridization solution (0.5 M disodium hydrogen-phosphate pH 7.2, 7% SDS, 1 mM EDTA) at 65° C. for 30 minutes to perform pre-hybridization.

Next, hybridization was performed using a probe that had been labeled with DIG (digoxigenin) by PCR using a DIG luminescence detection kit and the MdTFL gene as a template. Specifically, hybridization was performed by immersing the membrane in a buffer solution for hybridization (0.5 M disodium hydrogen-phosphate pH 7.2, 7% SDS, 1 mM EDTA) containing the labeled PCR probe at 65° C. for 16 hours. Then, the membrane was washed three times in a phosphate buffer (40 mM disodium hydrogen phosphate pH 7.2, 7% SDS, 1 mM EDTA) at 65° C. for 20 minutes, thereby performing an antibody reaction for detection. After the reaction, autoradiogram was taken, so that a band hybridizing to the probe was examined. The results are shown in FIG. 1.

Among restriction enzymes used for digestion of DNA, the cleavage sites of NcoI, XbaI and XhoI were not present within the probe, and minor bands were also observed in addition to major bands, suggesting the presence of another gene having relatively high homology with the target MdTFL gene.

Example 3

Northern Blot Analysis of MdTFL Gene (1) Preparation of RNA

Total RNA was prepared by the method described in Example 1 (2) above from each apple plant organs including calices, flower petals, stamens, pistils, shoot apices, leaves, cotyledons, stems and roots. In addition, shoot apices and flower-bud portions of the apple plants were collected from June to April of the following year at preset intervals, and then total RNAs of the shoot apices of the flower buds collected at each time were prepared.

(2) Hybridization

10 μg of the total RNA obtained in (1) above was subjected to formaldehyde denaturation 1.2% agarose gel electrophoresis, and then transferred to a nylon membrane. The membrane was immersed in a pre-hybridization solution (5×SSC, 10×Denhardt's solution, 10 mM $Na_2PO_4$ (pH 6.5), 0.5% SDS, 50% formamide, 10 mg/mL salmon sperm DNA) at 65° C. for 1 hour to perform pre-hybridization. Subsequently, hybridization was performed using an RNA probe that had been labeled with DIG (digoxigenin) by in vitro reverse transcription reaction using a DIG-RNA labelling kit and the MdTFL gene (SEQ ID NO: 1) as a template. Specifically, hybridization was performed by immersing the membrane in a hybridization buffer containing DIG-labeled RNA probe at 65° C. for 16 hours. Subsequently, the membrane was washed twice in 2×SSC containing 0.1% SDS at room temperature for 15 minutes, and then washed twice in 0.2×SSC containing 0.1% SDS at 65° C. for 15 minutes. After an antibody reaction was performed for detection, autoradiogram was taken to examine for bands hybridizing to the probe. The results are shown in FIGS. 2 and 3.

Figure 2:
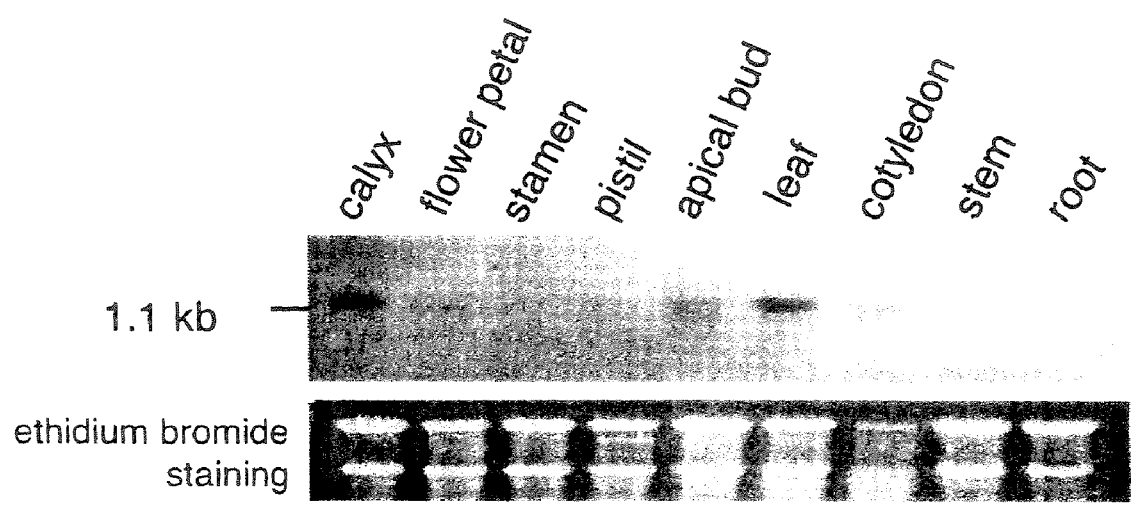
FIG. 2 provides a photograph of electrophoresis showing expression of the MdTFL gene in each tissue of non-transformed apple plants as detected by the Northern blotting.
Figure 3:
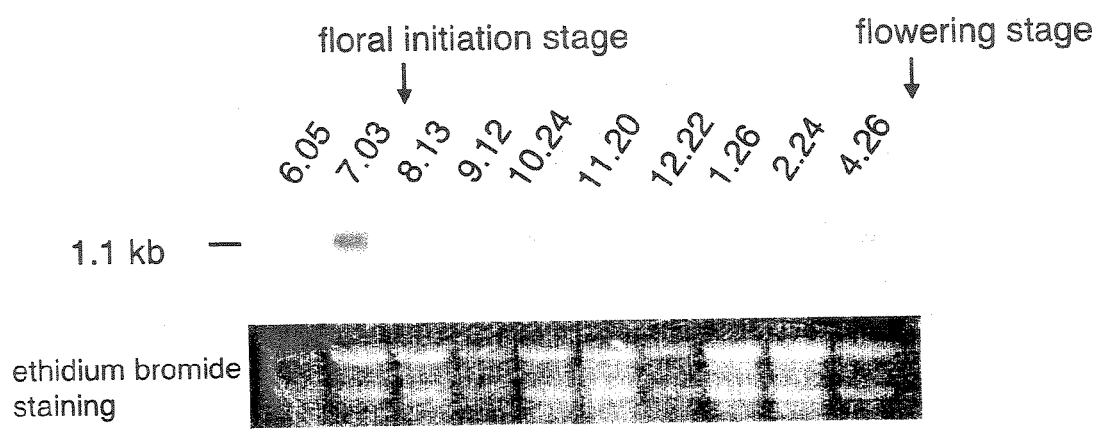
FIG. 3 provides a photograph of an electrophoresis showing the expressions of the MdTFL gene over time in the shoot apices from the current shoots of a non-transformed apple plant, as detected by the Northern blotting.

Expression of the MdTFL gene was observed among the organs of the apple plants: calyx, leaf and shoot apex portions (FIG. 2). Further, concerning expression pattern in different seasons observed for the shoot apex portion of the flower bud of the apple plants, strong expression was observed in the latter half of June which corresponds to just before the floral initiation stage. Afterwards, a tendency of a gradual decrease in expression levels was observed (FIG. 3).

Example 4

Gene Transfer to Plant (Transformation)

(1) Construction of Plasmid for Plants pBMDTFL12 (1 μg) obtained in Example 1 above wherein the MdTFL gene had been introduced in a sense orientation was cleaved in L buffer (10 mM Tris-HCl (pH 7.5), 10 mM $MgCl_2$, 1 mM dithiothreitol) at 37° C. using KpnI (3 units), and then cleaved in K buffer (20 mM Tris-HCl (pH 7.5), 10 mM $MgCl_2$, 1 mM dithiothreitol, 100 mM NaCl) at 30° C. using BamHI (3 units) for 2 hours each to obtain an approximately 650 bp DNA fragment containing the MdTFL gene. On the other hand, plasmid vector pUC119 was cleaved with similar restriction enzymes, and ligated to the gene using a ligation kit to construct pUMDTFL12.1+. The obtained pUMDTFL12.1+ was transformed into *Escherichia coli* DH5α.

The resulting transformant was cultured, and then pUMDTFL12 was purified from the culture medium. Subsequently, pUMDTFL12.1+ (10 μg) was cleaved in M buffer (10 mM Tris-HCl (pH 7.5), 10 mM $MgCl_2$, 1 mM dithiothreitol, 50 mM NaCl) using XbaI (30 units) and SacI (30 units) at 37° C. for 12 hours to obtain approximately 650 bp of a DNA fragment containing the MdTFL gene. On the other hand, binary vector pSMAK251 (10 μg) carrying CaMV35S promoter DNA was treated in the similar manner to the above procedures using XbaI (30 units) and SacI (30 units) to remove GUS region. The above approximately 650 bp DNA fragment containing MdTFL and pSMAK251 were ligated using a Ligation Kit (TAKARA) at 4° C. for 16 hours. The thus obtained ligation product was transformed to *Escherichia coli* in the similar manner to the above procedures. The thus obtained transformant was cultured, and then pSMDTFL12.1.2+ was purified from the culture. Binding of pSMDTFL12.1.2+ in a sense orientation was confirmed by cleavage with SacI (FIG. 4A).

Figure 4:
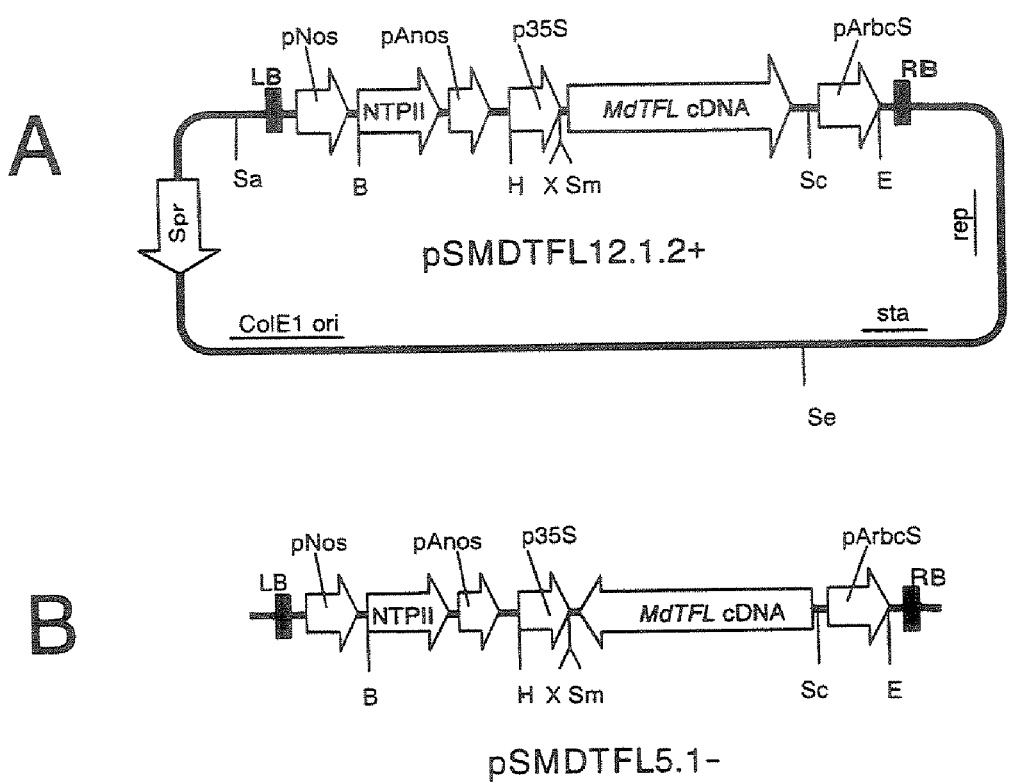
FIGS. 4A and 4B show the binary vectors pSM-DTFL12.1.2+ and pSMDTFL5.1−, respectively, which are used for the transformation of Arabidopsis and apple plants in the present invention.

Next, to prepare a binary vector carrying the MdTFL gene in an antisense orientation, a procedure was performed in the similar manner to the above using plasmid pBMDTFL5 wherein MdTFL gene had been introduced in an antisense orientation to obtain pSMDTFL5.1−. pSMDTFL5.1− was cleaved with SacI, so that the binding in an antisense orientation was confirmed (FIG. 4B).

(2) Preparation of *Agrobacterium* Containing Plasmids pSMDTFL12.1.2+ and pSMDTFL5.1−

The plasmids pSMDTFL12.1.2+ and pSMDTFL5.1− for plants obtained in (1) above were introduced into *Agrobacterium tumefaciens* strain EHA101 (E. E. Hood et al., The hypervirulence of *Agrobacterium tumefaciens* A281 is encoded in a region of a TiBo542 outside of T-DNA, J. Bacteriol. 168 (1986) 1291-1301) by a freezing and thawing method. Specifically, *Agrobacterium* strains were cultured at 28° C. overnight in 500 mL of ψB medium (2% Bactotrypton, 0.5% Bactoyeast extract, 1.0% $MgSO_4$, pH 7.2). When optical density at 650 nm (O.D. 650) reached 1.0, the cells were collected, and then centrifuged at 6000×g for 5 minutes. The pellet was washed with 100 mL of LB medium, centrifuged in a similar manner to the above procedure, and then the pellet was re-suspended in 25 mL of LB medium. 200 μl of the suspension was respectively poured into 1.5 mL tubes, and then the suspensions were stored at −80° C., thereby obtaining competent cells.

200 μl of the competent cells, a purified pSMDTFL12.1.2+ or pSMDTFL5.1− plasmid (5 μg) and 100 μl of LB medium were mixed. The mixed solution was allowed to stand in liquid nitrogen for 5 minutes. After the solution was incubated at 37° C. for 25 minutes, 15 mL of LB medium was added to the solution. The thus obtained suspension of transformed *Agrobacterium* strain was allowed to stand at 28° C. overnight in an incubator.

The suspension was centrifuged at 6000×g for 5 minutes to collect the cells. The pellet was suspended in 300 μl of LB medium, and then 100 μl of the above *Agrobacterium* suspension was applied onto an LB agar plate containing antibiotics (100 μg/mL spectinomycin (Japanese Trade Name: Trobicin), 50 μg/mL streptomycin). The suspension was cultured at 28° C. for 2 days, so that *Agrobacterium* strains having pSMDTFL12.1+ introduced and *Agrobacterium* strains having pSMDTFL5.1− introduced therein were obtained respectively.

(3) Infection of *Arabidopsis thaliana* with *Agrobacterium* Strains

*Arabidopsis thaliana* was infected with *Agrobacterium* strains by a floral dip method. Specifically, the zygotes of the transformed *Agrobacterium* strains obtained in (2) above were cultured in ψB medium (10 mL) containing 100 μg/mL spectinomycin at 28° C. until O.D. at 600 nm reached 0.8. The culture medium was centrifuged to remove the medium, and then 5% sucrose solution was added and suspended for O.D. at 600 nm to be 0.8. Next, Silwet 77 (Nippon Unicar Co., Ltd.) was added at a final concentration of 0.02% to 0.05% (v/v), thereby preparing a treatment solution.

On the other hand, about 20 *Arabidopsis* plants (Columbia) were grown for 3 weeks in 7 cm pots containing soil wherein equal amount of perlite and vermiculite had been mixed. Then, *Agrobacterium* strain was infected to the plants by immersing the *Arabidopsis* buds after flower stalk formation in the above *Agrobacterium* treatment solution containing plasmid pSMDTFL12.1.2+ or pSMDTFL5.1− for 3 seconds. The pots were transferred onto a tray, covered with cups for 1 day to maintain humidity. The plants were grown intact to obtain seeds. Seeds were sterilized using 2.5% sodium hypochlorite aqueous solution containing 0.05% Tween 20, and then inoculated on an agar prepared by adding 25 mg/mL kanamycin to ½ MS medium for selection. *Arabidopsis* plants that had grown on the selection medium were transferred to pots, thereby obtaining *Arabidopsis* transformants.

The seeds were then inoculated onto select ion media in a similar manner to obtain their progenies.

(4) Infection of Apple Leaves with *Agrobacteria*

A tissue culture line of Apple (*Malus* x *domestica*) var. "Ohrin" was sub-cultured in MS media containing 1 mg/mL 6-benzylaminopurine, 0.1 mg/mL 3-indoleacetic acid and B5 vitamin per liter of the medium. After approximately 1 month, the leaves that had developed were obtained.

Approximately 5 mm×10 mm sections were prepared from the leaves, and cultured overnight at 28° C. Then, *Agrobacterium* solution containing pSMDTFL5.1− was added to the leaf sections for *Agrobacterium* strains to infect for 30 minutes. Subsequently, the leaf sections were transferred onto MS media, and then co-cultured for 1 week.

(5) Selection of Transformed Cells and Regeneration into Plant

After co-culturing, the leaf sections were transferred to selection media (the above MS medium supplemented with 3.38 mg/mL 6-benzylaminopurine, 0.93 mg/mL α-naphthyl acetate, 500 µg/mL cefotaxime and 25 µg/mL kanamycin), cultured in darkness at 25° C. for 2 weeks, and then cultured with a cycle of 16 hours in light and 8 hours in darkness. About 1 to 2 months later, kanamycin-resistant adventitious buds formed on calli were obtained as transformants.

The obtained adventitious buds were sub-cultured, and then the leaves that had developed were collected. DNA was extracted from the leaves, and then the presence of the transgene, MdTFL, was confirmed by PCR. Specifically, PCR was performed using as a template the above DNA and as primers the sense primer (2S) and the antisense primer (2A) prepared in (6) above. PCR reaction was performed 40 cycles with each cycle consisting of the following conditions: thermal denaturation at 94° C. for 1 minute, annealing at 50° C. for 1 minute, and extension reaction at 72° C. for 2 minutes. The composition of PCR reaction solution is as follows.

| | |
|---|---|
| DNA solution | 1 µl |
| Sterile distilled water | 17.5 µl |
| 10× PCR buffer | 2.5 µl |
| 2.5 mM dNTP mix | 2 µl |
| 10 µM sense primer | 1 µl |
| 10 µM antisense primer | 1 µl |
| 5 U/µl Taq polymerase | 0.25 µl |
| Total | 25.25 µl |

(6) Naturalization of Transformant

After gene transfer was confirmed by PCR using specific primers, naturalization of the individual plants having MdTFL gene introduced therein in (4) above was performed by grafting cultured shoots onto rootstocks. The thus obtained recombinant apple plants were transferred to an isolated greenhouse, and then cultivated for trait evaluation.

Example 5

Figure 5:
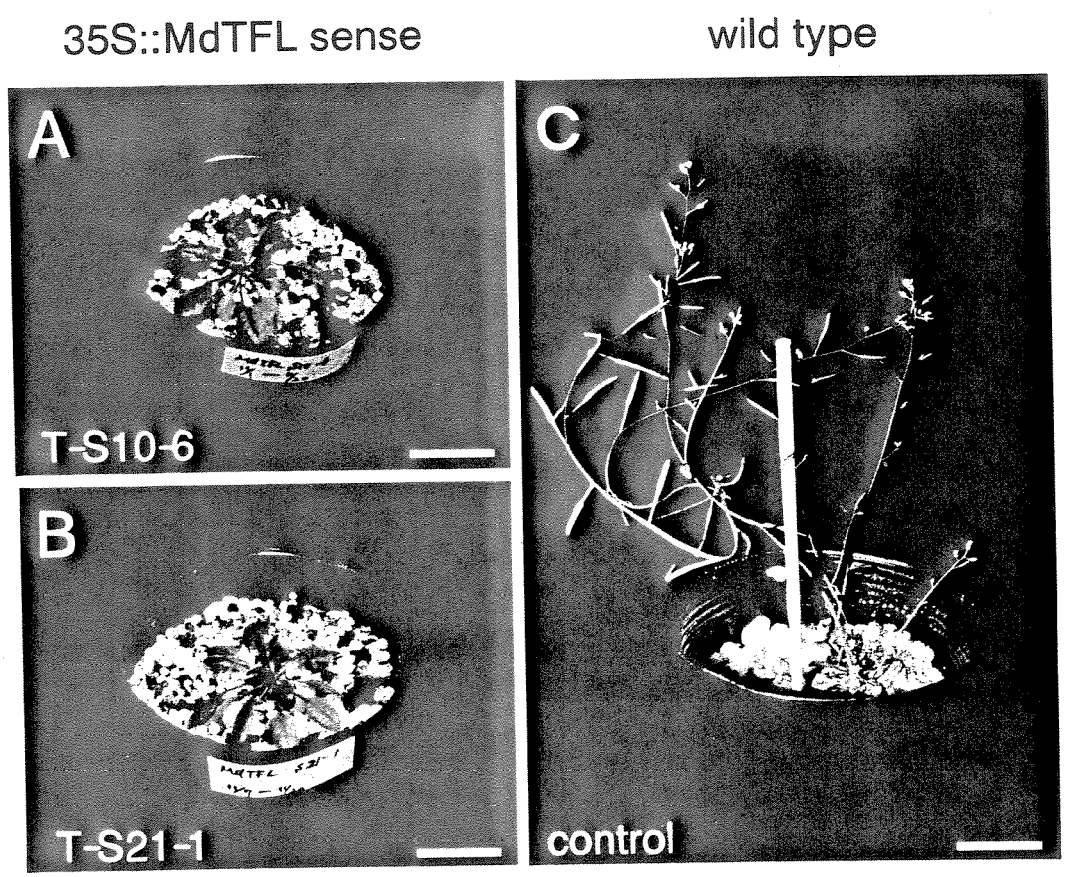
FIGS. 5A and 5B provide photographs showing the growth of transformed Arabidopsis plants having the MdTFL sense introduced therein (lines T-S10-6 and T-S21-1, respectively).
FIG. 5C shows a photograph showing the growth of wild type Arabidopsis plant as control. These photographs in FIGS. 5A to 5C were taken at 35 days after sowing.

Morphological Analysis of Transformed Plant (1) Morphological Analysis of *Arabidopsis* Transformants Having the Sense and the Antisense of the MdTFL Gene Introduced Therein 31 lines of *Arabidopsis* having the sense of the MdTFL gene introduced therein were obtained and 6 lines of *Arabidopsis* having the antisense of the MdTFL gene introduced therein were obtained (T1 generation). Further, the progenies of each line were obtained (T2 generation). Late flowering was observed for 6 lines out of 31 lines of *Arabidopsis* transformants having the sense gene, pSMDTFL12.1.2+, introduced therein. Further, T2 generation was obtained from these 6 lines, and then cultivated under long-day conditions (16 hours in light and 8 hours in darkness), so that the time to flowering was monitored (FIG. 5 and Table 1).

TABLE 1

Flowering time, rosette leaves and T2 generation of *Arabidopsis* transformants having the sense of the MdTFL gene

| transformant line (T1) | days needed for flowering | N of rosette leaves upon flowering | N of progenies obtained(T2) |
|---|---|---|---|
| Control (WT) | 30.3 ± 1.6 | 8.0 ± 1.0 | 10 |
| T-S6 | 39.4 ± 5.1 | 11.8 ± 3.6 | 5 |
| T-S10 | 59.0 ± 15.6 | 15.6 ± 4.3 | 5 |
| T-S11 | 45.4 ± 6.0 | 11.8 ± 2.3 | 5 |
| T-S21 | 44.7 ± 6.9 | 18.0 ± 4.3 | 3 |
| T-S22 | 47.0 ± 0 | 23.0 ± 4.6 | 3 |
| T-S28 | 53.0 ± 6.0 | 21.5 ± 1.5 | 2 |

While the control plant, wild type *Arabidopsis thaliana* flowered within 30 days on average, flowering of the transformants was delayed by approximately 9 to 29 days.

Figure 6:
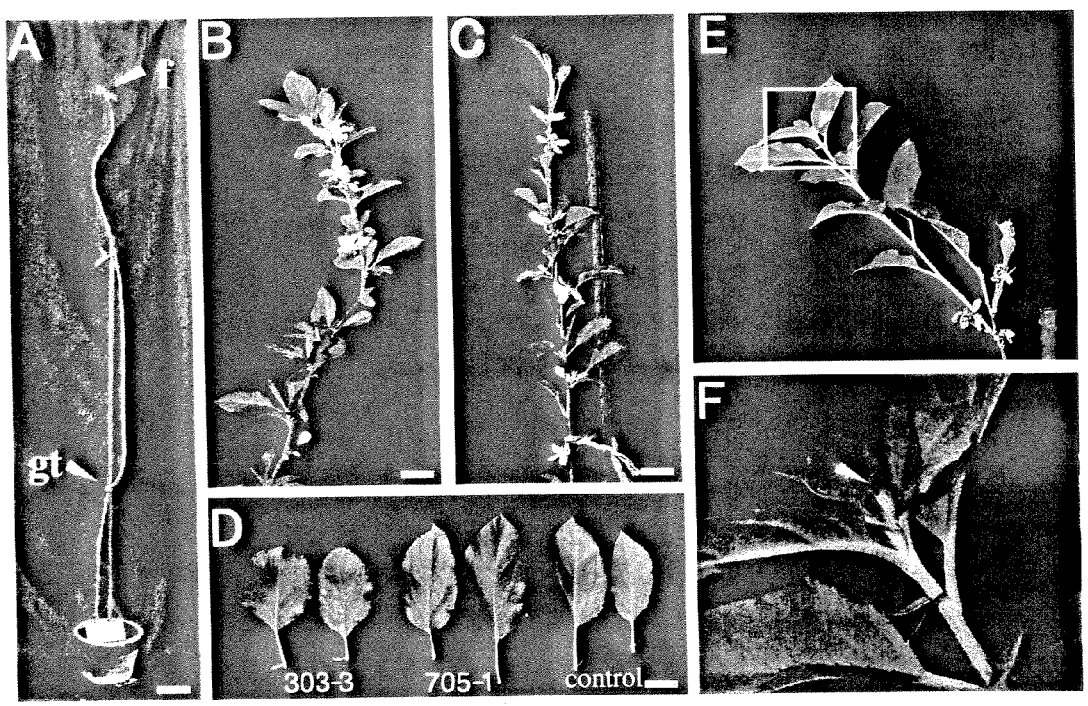
FIGS. 6A to 6F show early flowered apple transformants.

(2) Morphological Analysis of Apple Transformants Having Antisense of MdTFL Gene Introduced Therein Ten apple transformants of 3 lines having the antisense of MdTFL gene introduced therein (lines 303-1, 303-2, 303-3, 303-4, 614-1, 614-2, 705-1, 705-2, 705-3 and 705-4) were obtained. Of these transformants, early flowering was observed within 8 to 15 months after grafting for lines 303-1, 303-4, 705-1, 705-2, 705-3 and 705-4 (FIG. 6 and Table 2).

TABLE 2

Time to flowering and pollen germination ability of apple transformants having antisense of MdTFL gene

| line | expression of transgene | months | germination ability | grafting time (year, month) |
|---|---|---|---|---|
| control | none | − | − | 1997 August |
| 303-1 | +++ | 11 | not tested | 2000 June |
| 303-2 | ++ | − | − | 2000 June |
| 303-3 | ++ | − | − | 2000 June |
| 303-4 | +++ | 11 | not tested | 2000 June |
| 705-1 | +++ | 8 | + | 2000 April |
| 705-2 | ++ | 15 | + | 2000 April |
| 705-3 | + | 11 | + | 2000 June |
| 705-4 | + | 11 | + | 2000 June |
| 614-1 | not tested | − | − | 2001 June |
| 614-2 | not tested | − | − | 2001 June |
| 614-3 | not tested | − | − | 2001 June |

In Table 2, "line" means transformant line, "months" means months needed after grafting to flowering, and "germination ability" means pollen germination ability. The "+++", "++" and "+" in the column "expression of transgene" indicate relatively strong expression, moderate expression, and expression is detected, respectively.

The non-transformants, 6-year-old Orin, cultivated as controls, did not flower even after 61 months. On the other hand, line 705-1 flowered at 8 months after grafting (FIG. 6A). Comparison with apple non-transformants revealed that the number of flowers of early flowering lines (transformants) tended to be as few as 1 or 2 per flower cluster on average, but the flowers were observed to be normal flower organs (FIGS. 7B and C) Concerning the leaf form, lines 303 tended to exhibit saw-tooth appearances in many cases to some extent, while there is no significant difference when lines 705 and the control Ohrin were compared (FIG. 6D).

Figure 7:
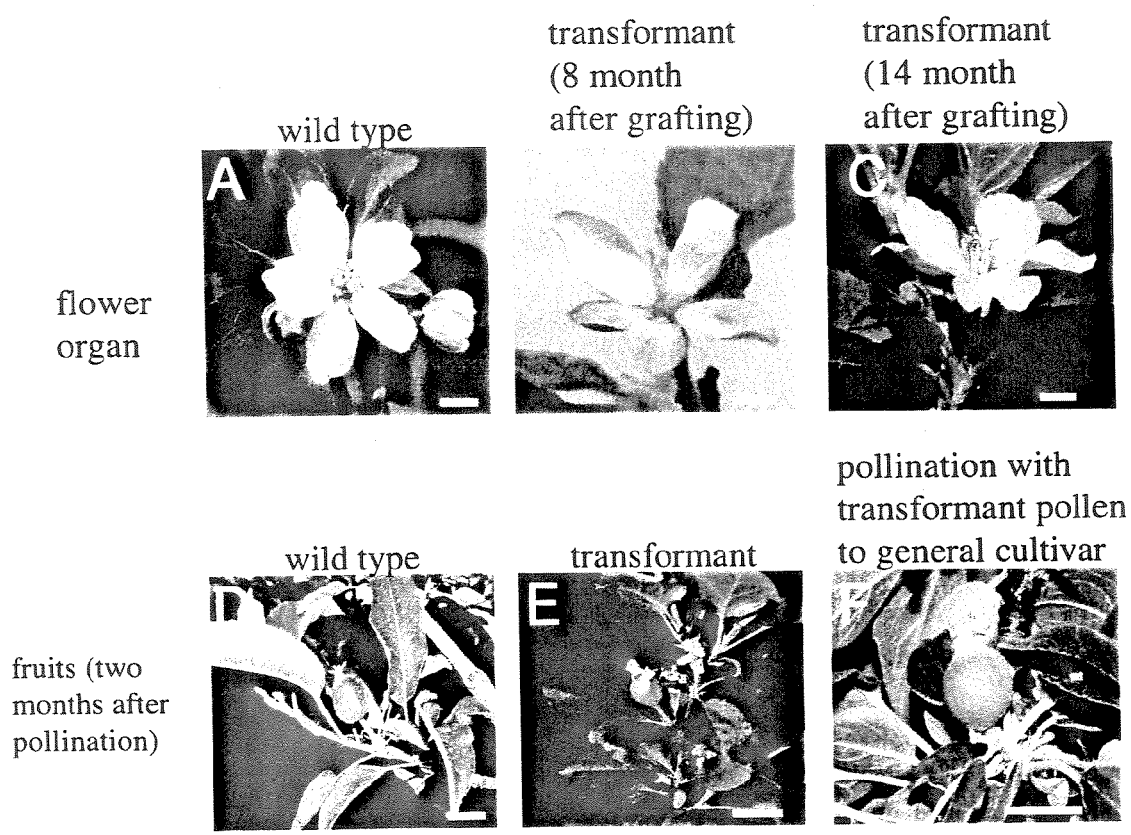
FIGS. 7A to 7C show photographs showing flowering of wild type apple plant and transformed apple plants having the MdTFL antisense introduced therein.
FIGS. 7D to 7F show photographs showing seed-setting of wild type apple plant and transformed apple plants having the MdTFL antisense gene introduced therein.
Figure 8:
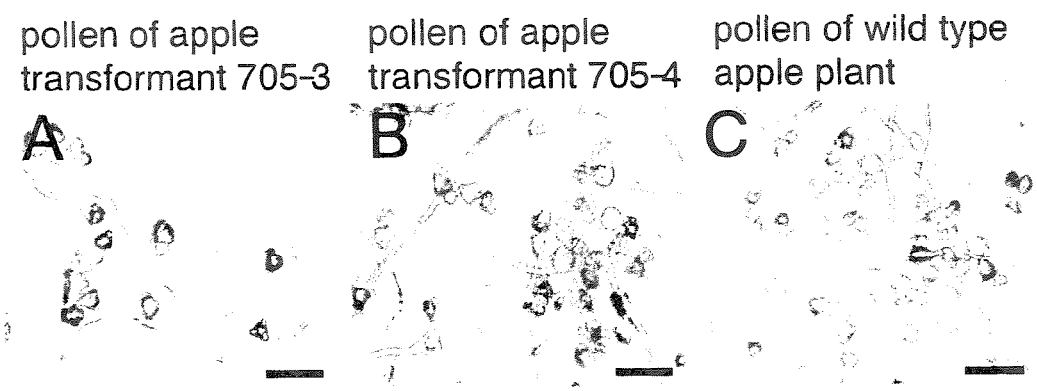
FIGS. 8A to 8C show photographs showing pollen germination ability of a transformed apple plant lines 705-3 and 705-4 that flowered early, and wild type apple plant, respectively.

Pollen fertility of early flowering lines was examined by crossing and a germination test on agar media. Crossing compatible varieties with early flowering lines led to seed setting. Further, crossing the pollens of early flowering lines with general varieties also led to seed setting, so that the presence of fertility was confirmed (FIG. 7 D to F). Pollens of all tested lines had germination ability (FIG. 8).

Example 6

Expression of MdTFL Gene in Apple Transformants

Total RNA was extracted from the transformant leaves having MdTFL gene introduced therein, and then Northern blot analysis was performed according to the above Example 3. A probe used herein was a sense RNA probe prepared by using the full-length MdTFL gene as a template. Bands were detected using LAS1000 (FUJI FILM).

Figure 9:
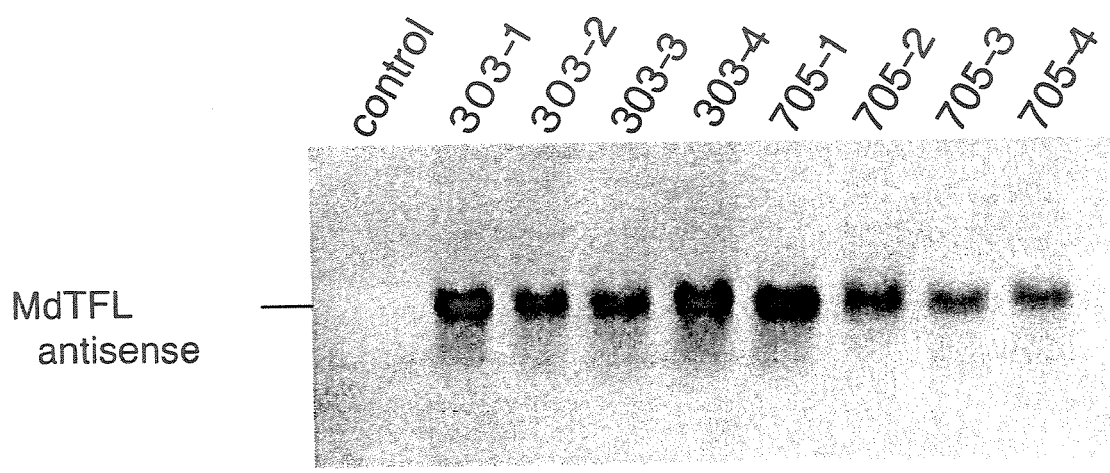
FIG. 9 provides a photograph of electrophoresis showing the expression of the transgene (MdTFL antisense) in the leaves of a wild type apple plant (control) and transformed apple plants (lines 303-1, 303-2, 303-3, 303-4, 705-1, 705-2, 705-3 and 705-4), as detected by the Northern blotting.

The obtained lines of apple transformants had a vector introduced therein wherein MdTFL gene had been ligated in an antisense orientation downstream of 35S promoter. It was confirmed by Northern blot analysis that antisense mRNA was over-expressed in all tested line (FIG. 9). Relatively high expression of antisense mRNA was observed in lines 303-1, 303-4 and 705-1, and these lines flowered early within a time period as short as 8 to 11 months after grafting (see Table 2).

While the invention has been described in detail with reference to certain preferred embodiments, it is appreciated that many variations and modifications may be made by those skilled in the art within the spirit and scope of the present invention as defined in the appended claims.

What is claimed is:

1. An antisense nucleic acid molecule complementary to all or a portion of SEQ ID NO:1 and
    wherein the antisense nucleic acid molecule can suppress or inhibit the expression of MdTFL gene of SEQ ID NO:1.

2. A recombinant vector, which comprises the antisense nucleic acid molecule of claim 1.

3. A transformant, which comprises the recombinant vector of claim 2, wherein the transformant is a plant or plant cell.

4. The transformant of claim 3, which has an early flowering property.

5. The transformant of claim 4, wherein the plant is a perennial plant.

6. The transformant of claim 5, wherein the perennial plant is a perennial fruit tree.

7. A seed comprising an antisense nucleic acid molecule complementary to all or a portion of SEQ ID NO:1 and
    wherein the antisense nucleic acid molecule can suppress or inhibit the expression of MdTFL gene of SEQ ID NO:1.

8. A method for conferring an early flowering property on a plant, comprising suppressing expression or activity of an endogenous MdTFL gene of SEQ ID NO:1 in a plant by introducing into said plant an antisense nucleic acid molecule which is complementary to all or a portion of SEQ ID NO:1 and
    wherein the antisense nucleic acid molecule can suppress or inhibit the expression of MdTFL gene of SEQ ID NO:1.

9. The method of claim 8, wherein the plant is a perennial plant.

10. The method of claim 9, wherein the perennial plant is a perennial fruit tree.

11. A method for regulating the time to flowering of a plant, comprising introducing the antisense nucleic acid molecule of claim 1 into a plant, whereby an early flowering phenotype is achieved.

12. The method of claim 11, wherein the plant is a perennial plant.

13. The method of claim 12, wherein the perennial plant is a perennial fruit tree.

14. A method for producing an early flowering plant, comprising constructing a recombinant vector comprising the antisense nucleic acid molecule of claim 1,
    transforming a host plant with the recombinant vector, and
    regenerating a plant from the transformed host plant.

15. The method of claim 14, wherein the plant is a perennial plant.

16. The method of claim 15, wherein the perennial plant is a perennial fruit tree.

* * * * *